(12) United States Patent  
Koyama et al.

(10) Patent No.: US 11,766,493 B2  
(45) Date of Patent: Sep. 26, 2023

(54) HEADGEAR CLEANER AND HEADGEAR STAND

(71) Applicant: CREATIVE TECHNOLOGY CORPORATION, Kawasaki (JP)

(72) Inventors: Satomi Koyama, Kawasaki (JP); Shinsuke Hirano, Kawasaki (JP); Yoshiaki Tatsumi, Kawasaki (JP)

(73) Assignee: CREATIVE TECHNOLOGY CORPORATION, Kanagawa (JP)

( * ) Notice: Subject to any disclaimer, the term of this patent is extended or adjusted under 35 U.S.C. 154(b) by 742 days.

(21) Appl. No.: 16/757,987

(22) PCT Filed: Nov. 7, 2018

(86) PCT No.: PCT/JP2018/041283  
§ 371 (c)(1),  
(2) Date: Apr. 21, 2020

(87) PCT Pub. No.: WO2019/098100  
PCT Pub. Date: May 23, 2019

(65) Prior Publication Data  
US 2020/0338222 A1    Oct. 29, 2020

(30) Foreign Application Priority Data  
Nov. 18, 2017    (JP) ................................ 2017-222341

(51) Int. Cl.  
*A61L 2/20* (2006.01)  
*A42C 3/04* (2006.01)  
(Continued)

(52) U.S. Cl.  
CPC ................ *A61L 2/202* (2013.01); *A42C 3/04* (2013.01); *A61L 9/015* (2013.01); *A42B 3/006* (2013.01);  
(Continued)

(58) Field of Classification Search  
CPC .......... A61L 2/202; A61L 9/015; A42B 3/006  
See application file for complete search history.

(56) References Cited

U.S. PATENT DOCUMENTS 8,038,963 B1    10/2011    Chen  
8,440,001 B2     5/2013    Cozean  
(Continued)

FOREIGN PATENT DOCUMENTS

CN        1277557 A    12/2000  
CN      102551489 A     7/2012  
(Continued)

OTHER PUBLICATIONS

China National Intellectual Property Administration, "Office Action with Search Report for Chinese Patent Application 201880069876.8," dated Dec. 29, 2020.  
(Continued)

*Primary Examiner* — Donald R Spamer  
*Assistant Examiner* — Priscilla Browning  
(74) *Attorney, Agent, or Firm* — Manabu Kanesaka

(57) ABSTRACT

Provided are a headgear stand and a headgear cleaner that is small-sized and has low power consumption, and that is capable of sterilizing and deodorizing headgear made of any material. A headgear cleaner 1-1 is provided with an ozone generator 2 and a voltage supply part 5. The ozone generator 2 is constituted from an ozone generator body 3-1 and a connecting part 4. The ozone generator body 3-1 forms a shape in which twelve leaf parts extend radially. The voltage supply part 5 supplies a voltage necessary for generating ozone to the ozone generator 2.

17 Claims, 19 Drawing Sheets

(51) Int. Cl.
*A61L 9/015* (2006.01)
*A42B 3/00* (2006.01)

(52) U.S. Cl.
CPC ........ *A61L 2202/11* (2013.01); *A61L 2202/26* (2013.01)

(56) References Cited

U.S. PATENT DOCUMENTS

| | | | |
|---|---|---|---|
| 2004/0071615 A1* | 4/2004 | Khatchatrian | A61Q 5/00 34/283 |
| 2013/0098753 A1 | 4/2013 | Sanematsu | |
| 2018/0147308 A1 | 5/2018 | Koyama et al. | |

FOREIGN PATENT DOCUMENTS

| | | |
|---|---|---|
| CN | 102960073 A | 3/2013 |
| CN | 104379010 A | 2/2015 |
| JP | 10-192798 A | 7/1998 |
| JP | H11-192287 A | 7/1999 |
| JP | 3067653 U | 4/2000 |
| JP | 2004-332142 A | 11/2004 |
| JP | 2005-152035 A | 6/2005 |
| JP | 3917105 B2 | 5/2007 |
| JP | 2017-064207 A | 4/2017 |
| TW | 571748 U | 1/2004 |
| TW | I466648 B | 1/2015 |
| WO | 99/20388 A2 | 4/1999 |
| WO | 01/19729 A2 | 3/2001 |
| WO | 2014/147459 A1 | 9/2014 |
| WO | 2016/190139 A1 | 12/2016 |

OTHER PUBLICATIONS

Taiwan Intellectual Property Office, "Office Action with Search Report for Taiwanese Patent Application 107140221," dated Nov. 3, 2022.
Europe Patent Office, "Search Report for European Patent Publication No. 18878713.9," dated Nov. 3, 2020.
PCT/ISA/210, "International Search Report for International Application No. PCT/JP2018/041283," dated Feb. 5, 2019.

* cited by examiner

HEADGEAR CLEANER AND HEADGEAR STAND

RELATED APPLICATIONS

The present application is National Phase of International Application No. PCT/JP2018/041283 filed Nov. 7, 2018, and claims priorities from Japanese Application No. 2017-222341, filed Nov. 18, 2017, the disclosure of which is hereby incorporated by reference herein in its entirety.

TECHNICAL FIELD

The present invention relates to a headgear cleaner and a headgear stand capable of sterilizing and deodorizing headgear such as a helmet, a hat, or a hairpiece.

BACKGROUND ART

Headgear such as helmets, hats, and hairpieces are commonly washed with water. Conventionally, as this type of technique, there is a headgear cleaner as described in, for example, Patent Literature 1.

The headgear cleaner includes a washing tank in which headgear such as a helmet is fixed and means for washing and drying the headgear.

With the arrangement above, sweat, sebum, odor, etc., adhering to the headgear are removed by a mechanical force of washing water flowing by an impeller and the chemical action of detergent mixed in the washing water.

As another technique, there has also been a headgear cleaner as described in, for example, Patent Literature 2.

The headgear cleaner includes an approximately semispherical mount base for mounting headgear thereon, ozone generating means for generating ozone, and a blower fan for blowing air containing generated ozone through a blower outlet. The cleaner then has a stand shape as a whole.

With the arrangement above, when the headgear cleaner is driven with headgear mounted on the mount base, the blower fan causes ozone generated in the ozone generating means to blow out through the blower outlet of the mount base with air, so that the inner surface of the headgear is sterilized and deodorized by the ozone.

CITATION LIST

Patent Literature

PLT 1: Japanese Application Laid-Open No. H10-192798
PLT 2: Japanese Utility Model No. 3067653

SUMMARY OF THE INVENTION

Technical Problem

However, the above-described conventional headgear cleaners suffer from the following problems.

First, the headgear cleaner in which headgear is washed with water and detergent requires equipment for supplying and draining water to/from the washing tank and power-supply equipment for drying, which problematically limits the site of installation of the headgear cleaner. In addition, the cleaner cannot be used for headgear made of leather, etc., that are prohibited from washing with water. It also suffers from a problem of reduced effectiveness in sterilization and deodorization due to washing with water.

On the other hand, the headgear cleaner in which headgear is sterilized and deodorized with ozone may not suffer from the problems from which the water-washing headgear cleaner suffers, but instead requires to be equipped therein with large-scale equipment such as a blower fan, resulting in an increase in size of the headgear cleaner itself. It is also necessary to supply high power from the power supply to the ozone generating means and the blower fan to drive them, suffering from a problem in power consumption.

The present invention has been made to solve the above-mentioned problems, and an object thereof is to provide a headgear cleaner and a headgear stand of small size and lower power consumption capable of sterilizing and deodorizing headgear made of any material.

Solution to the Problems

In order to solve the above-described problems, the invention of claim 1 provides a headgear cleaner including an approximately semispherical hull-shaped ozone generator formed of flexible material and capable of receiving headgear such as a helmet thereon and a voltage supply part for supplying a voltage required to generate ozone to the ozone generator, in which the ozone generator has a dielectric and one or more pairs of electrodes, at least one electrode of each pair of electrodes is covered with the dielectric, and the voltage supply part is arranged to supply a voltage required to generate ozone to the one or more pairs of electrodes of the ozone generator.

With the arrangement above, a user can put headgear such as a helmet on the approximately semispherical hull-shaped ozone generator or can put the approximately semispherical hull-shaped ozone generator inside of the headgear. At this time, if the interior of the headgear has an approximately semispherical shape, the ozone generator fits inside of the headgear. Even if the interior of the headgear does not have an approximately semispherical shape, the ozone generator, which is formed of flexible material, is deformed to follow the interior of the headgear and fit inside of the headgear.

In this state, when the voltage supply part is activated, a predetermined voltage is supplied to the one or more pairs of electrodes of the ozone generator, whereby ozone is released from the ozone generator.

At this time, since the surface of the ozone generator is proximal to the inner surface of the headgear, ozone released from the ozone generator sufficiently sterilizes and deodorizes the interior of the headgear.

That is, the headgear, regardless of the type of material, is sufficiently sterilized and deodorized by ozone released from the nearby ozone generator. For this reason, in the above-described conventional headgear, equipment such as a blower fan for blowing ozone was required. However, the headgear cleaner according to the present invention requires no additional devices and can accordingly have a reduced size and reduced power consumption.

In the invention of claim 2, the headgear cleaner according to claim 1 is arranged such that the ozone generator includes multiple leaf parts extending radially from a top portion and curved downward to have an approximately semispherical hull shape as a whole and a connecting part that is connected to lower end portions of the multiple circularly arranged leaf parts to keep the overall shape of the multiple leaf parts in the approximately semispherical hull shape.

With the arrangement above, adjacent ones of the leaf parts can be brought close to or steered away from each other to adjust the diameter of the ozone generator, whereby headgear of various sizes can be put on the ozone generator for sterilization and deodorization.

In the invention of claim 3, the headgear cleaner according to claim 2 is arranged such that the ozone generator can be developed, by detaching the connecting part, into a planar shape in which the multiple leaf parts extend radially from a central portion that corresponds to the top portion.

With the arrangement above, the headgear cleaner can have a further reduced overall size when not being used by developing the ozone generator into a planar shape. It is consequently possible to save space for storing the headgear cleaner when not being used.

The headgear cleaner can also be used with the ozone generator developed in a planar shape to sterilize and deodorize not only three-dimensional headgear but also two-dimensional headgear.

In the invention of claim 4, the headgear cleaner according to claim 1 is arranged such that the ozone generator includes multiple leaf parts having multiple circularly connected lower end portions and curved upward to have an approximately semispherical hull shape as a whole and a connecting part that connects all upper end portions of the multiple leaf parts at a top portion and connects specific adjacent ones of the leaf parts to keep the overall shape of the multiple leaf parts in the approximately semispherical hull shape.

In the invention of claim 5, the headgear cleaner according to claim 4 is arranged such that the ozone generator can be developed, by detaching the connecting part, into a planar shape in which the multiple leaf parts are arranged laterally with the multiple lower end portions connected.

In the invention of claim 6, the headgear cleaner according to claim 1 is arranged such that the ozone generator includes multiple annular parts and a connecting part connecting the annular parts, the annular parts are each set to have a lower opening portion with a size greater than that of an upper opening portion, the lower opening portion of an upper one of the annular parts is set to have a size approximately equal to that of the upper opening portion of a lower one of the annular parts that is connected to the upper annular part, the multiple annular parts are disposed in series downward from a top part with the lower opening portion of the upper annular part fitted on the upper opening portion of the lower annular part, and the connecting part connects the upper annular part and the lower annular part in a manner movable up and down.

With the arrangement above, a user can put headgear such as a helmet on the approximately semispherical hull-shaped ozone generator or can put the approximately semispherical hull-shaped ozone generator inside of the headgear. At this time, the upper annular part and the lower annular part can be moved up and down to connect the multiple annular parts using the connecting part and thereby freely adjust the depth of the ozone generator.

In the invention of claim 7, the headgear cleaner according to any one of claims 1 to 6 is arranged such that the dielectric of the ozone generator is formed of polymeric resin having a permittivity equal to or higher than 3 and a dielectric breakdown voltage equal to or higher than 15 kV/mm.

With the arrangement above, the ozone generator is made of robust material that can withstand high voltage and easily generate plasma for ozone generation.

In the invention of claim 8, the headgear cleaner according to any one of claims 1 to 7 is arranged such that a spacer is provided on the surface of the ozone generator for keeping the distance between the surface of the ozone generator and the inner surface of the headgear equal to or smaller than 10 mm.

With the arrangement above, even headgear having, for example, a rough inner surface or an inner surface cloth which is difficult to sterilize and deodorize, can be sterilized and treated reliably and effectively.

In the invention of claim 9, the headgear cleaner according to claim 8 is arranged such that the spacer is a protrusion provided in a manner protruding from the surface of the ozone generator and having a height equal to or smaller than 10 mm.

In the invention of claim 10, the headgear cleaner according to claim 8 is arranged such that the spacer is a linear object attached to the surface of the ozone generator and having a height equal to or smaller than 10 mm.

In the invention of claim 11, the headgear cleaner according to any one of claims 1 to 10 is arranged such that the pair of electrodes of the ozone generator are each formed in a comb shape and comb teeth of each of the pair of electrodes are engaged with each other at regular intervals.

In the invention of claim 12, the headgear cleaner according to any one of claims 1 to 10 is arranged such that one electrode of each pair of electrodes of the ozone generator is housed in the dielectric, while the other electrode, having a number of holes or a comb shape, is disposed on the dielectric facing the one electrode.

A headgear stand according to the invention of claim 13 includes headgear receiving part with the surface of an upper portion thereof having an approximately semispherical shape and capable of receiving headgear such as a helmet thereon, a self-standing support part having an upper portion capable of supporting the headgear receiving part thereon, and a headgear cleaner according to any one of claims 1 to 12, in which the ozone generator is mounted on the headgear receiving part and the voltage supply part is disposed in the support part.

With the arrangement above, when headgear is put on the headgear receiving part with the support part standing, the ozone generator of the headgear cleaner is arranged inside of the headgear, so that the headgear is held reliably on the headgear receiving part.

In this state, when the voltage supply part, which is disposed in the support part, is activated, a predetermined voltage is supplied to the one or more pairs of electrodes of the ozone generator, whereby ozone is released from the ozone generator.

As a result, ozone is released against the inner surface of the headgear, whereby the interior of the headgear is to be sterilized and deodorized.

Effects of the Invention

As described above in detail, the present invention exhibits an advantageous effect that headgear, regardless of the type of material, can be sufficiently sterilized and deodorized by ozone released from the nearby ozone generator, whereby the headgear cleaner requires no additional device such as a blower fan for ozone blowing and can accordingly have a reduced size and reduced power consumption.

The inventions of claims 2 and 4 exhibit an effect that headgear of various sizes can be sterilized and deodorized.

The inventions of claims 3 and 5 exhibit an effect that the headgear cleaner can have a further reduced overall size and it is consequently possible to save space for storing the headgear cleaner when not being used and also to sterilize and deodorize not only three-dimensional headgear but also two-dimensional headgear.

The invention of claim 6 exhibits an effect that the depth of the ozone generator can be adjusted freely.

The invention of claim 7 exhibits an effect that the ozone generator is made of robust material that can withstand high voltage and easily generate plasma for ozone generation.

The invention of claim 8 exhibits an effect that even headgear that is difficult to sterilize and deodorize can be sterilized and deodorized reliably and effectively.

DESCRIPTION OF THE EMBODIMENTS

The best modes of the present invention will hereinafter be described with reference to the accompanying drawings.

First Embodiment

Figure 1:
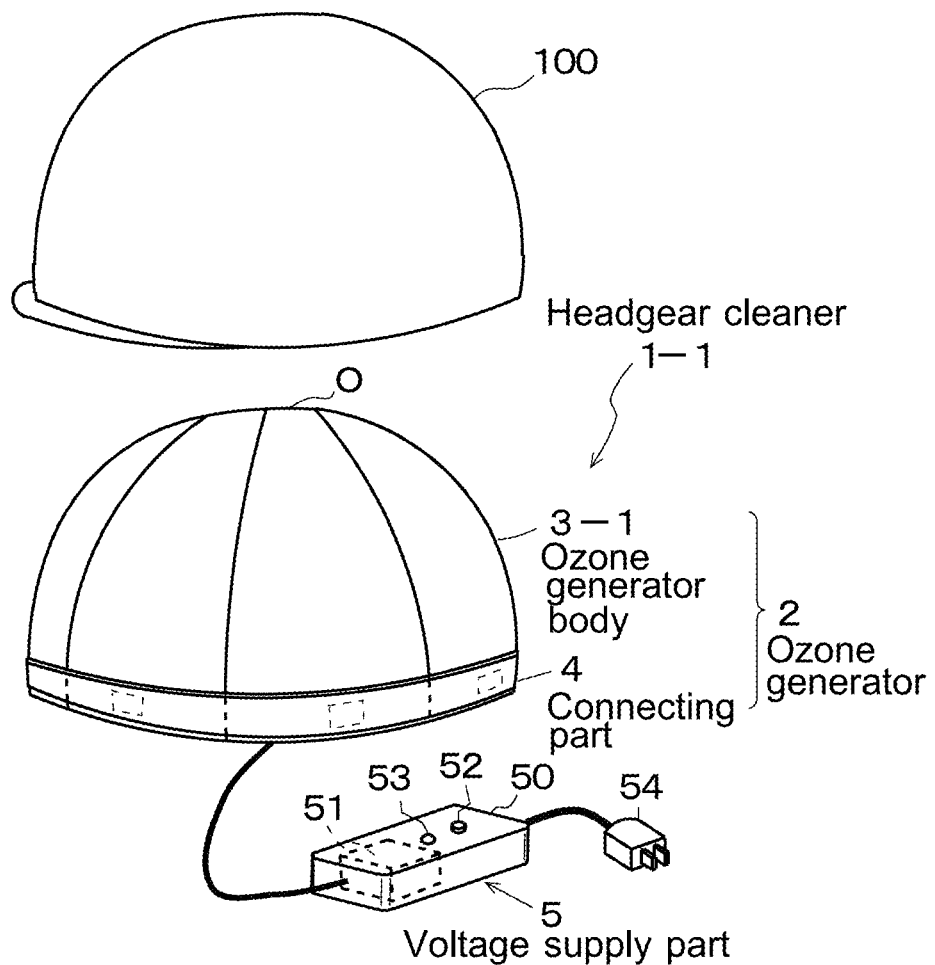
FIG. 1 is a perspective view showing a headgear cleaner according to a first embodiment of the present invention.
Figure 2:
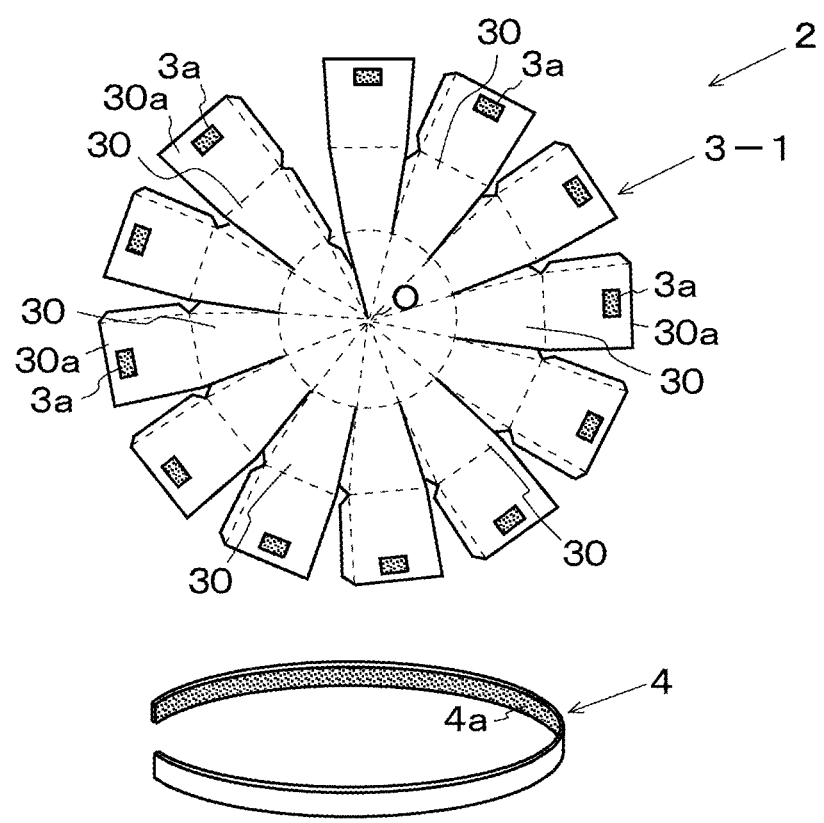
FIG. 2 is a structural view showing a developed ozone generator body.

FIG. 1 is a perspective view showing a headgear cleaner according to a first embodiment of the present invention and FIG. 2 is a structural view showing a developed ozone generator body.

As shown in FIG. 1, the headgear cleaner 1-1 of this embodiment includes an ozone generator 2 and a voltage supply part 5.

The ozone generator 2 is an approximately semispherical hull-shaped member for receiving headgear thereon. While a helmet, a hat, and a hairpiece, for example, may be offered as the headgear, this embodiment exemplifies a helmet 100 as the headgear.

The ozone generator 2 is composed of an ozone generator body 3-1 and a connecting part 4 with a structure in which the shape of the ozone generator body 3-1 is kept by the connecting part 4.

Specifically, as shown in FIG. 2, the ozone generator body 3-1 can be developed into a planar shape by detaching the connecting part 4 from the ozone generator body 3-1. In this developed state, the ozone generator body 3-1 has a shape in which twelve leaf parts 30 of the same shape extend radially from a central portion O.

Figure 3:
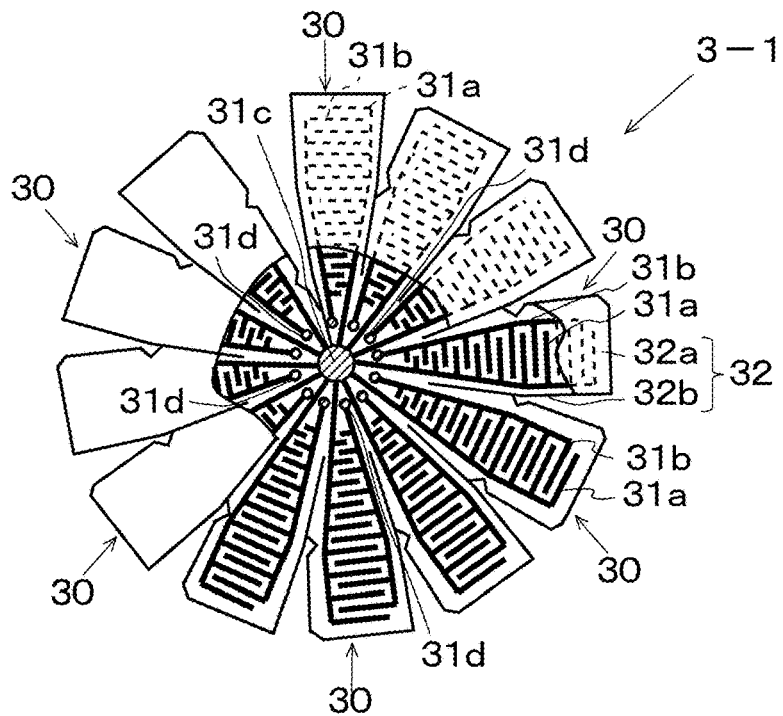
FIG. 3 is a partially-cutaway schematic plan view showing the developed ozone generator body.
Figure 4:
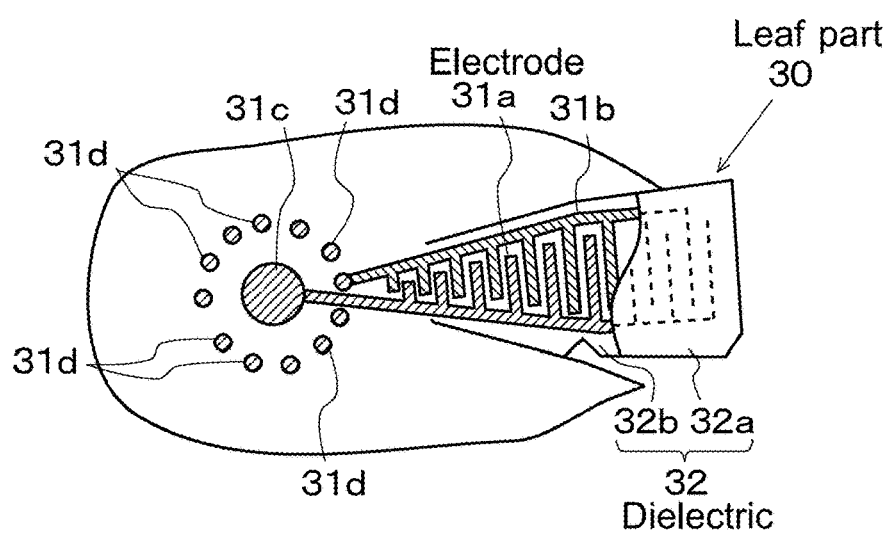
FIG. 4 is a partially-enlarged view showing the structure of a pair of electrodes.

FIG. 3 is a partially-cutaway schematic plan view showing the developed ozone generator body and FIG. 4 is a partially-enlarged view showing the structure of a pair of electrodes.

As shown in FIG. 3, each leaf part 30 is formed by a sheeted dielectric 32 and a pair of electrodes 31*a*, 31*b* covered with the dielectric 32.

Specifically, the dielectric 32 is composed of two dielectric layers 32*a*, 32*b*, and the pair of electrodes 31*a*, 31*b* are formed on the lower dielectric layer 32*b*, on which the upper dielectric layer 32*a* is laminated to cover the electrodes 31*a*, 31*b*.

The ozone generator body 3-1 having the thus arranged twelve leaf parts 30 is entirely formed of flexible polymeric resin.

Specifically, the dielectric layers 32a, 32b are each formed of polymeric resin having a permittivity equal to or higher than 3 and a dielectric breakdown voltage equal to or higher than 15 kV/mm (kilovolt/millimeter). In this embodiment, such polymeric resin employs any one of polyimide, silicone, PET (polyethylene terephthalate), and vinyl chloride. Each pair of electrodes 31a, 31b are also formed of conductive polymer, a kind of polymeric resin.

Also, as shown in FIG. 4, the pair of electrodes 31a, 31b are each formed in a comb shape. That is, multiple comb teeth are engaged with each other at regular intervals. All of the twelve electrodes 31a are then connected to one terminal 31c provided in the central portion of the ozone generator body 3-1 on the dielectric layer 32b, while the twelve electrodes 31b are connected, respectively, to twelve terminals 31d disposed around the terminal 31c, also as shown in FIG. 3.

The thus structured ozone generator body 3-1 has a Velcro tape (registered trademark) piece 3a on the surface of a lower end portion 30a of each leaf part 30, as shown in FIG. 2.

On the other hand, the connecting part 4 is a belt-shaped body with a Velcro tape 4a attached to approximately the entire inside thereof.

Thus, the ozone generator body 3-1 can be formed to have an approximately semispherical hull shape as a whole by curving all the leaf parts 30 toward the interior surface in FIG. 2 such that the lower end portions 30a of the twelve leaf parts 30 are arranged circularly. In this state, when the connecting part 4 is wound around the lower end portions 30a of the circularly arranged leaf parts 30 with the Velcro tape 4a side facing the ozone generator body 3-1 side, the Velcro tape pieces 3a and the Velcro tape 4a are fastened to keep the overall shape of the ozone generator body 3-1 in the approximately semispherical hull shape.

Figure 5:
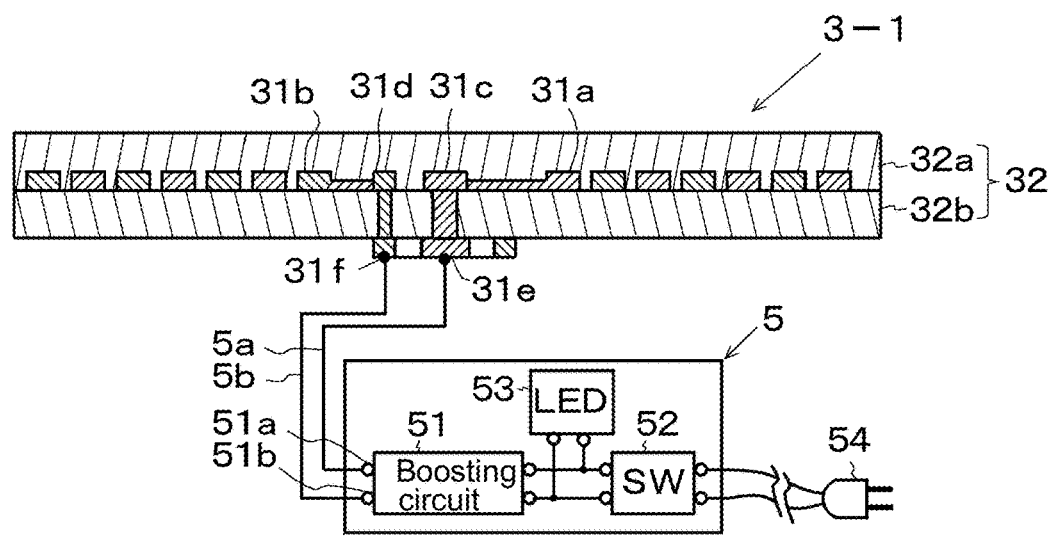
FIG. 5 is an electrical wiring diagram showing the connection between the cross-sectionally shown ozone generator body and a voltage supply part.
Figure 6:
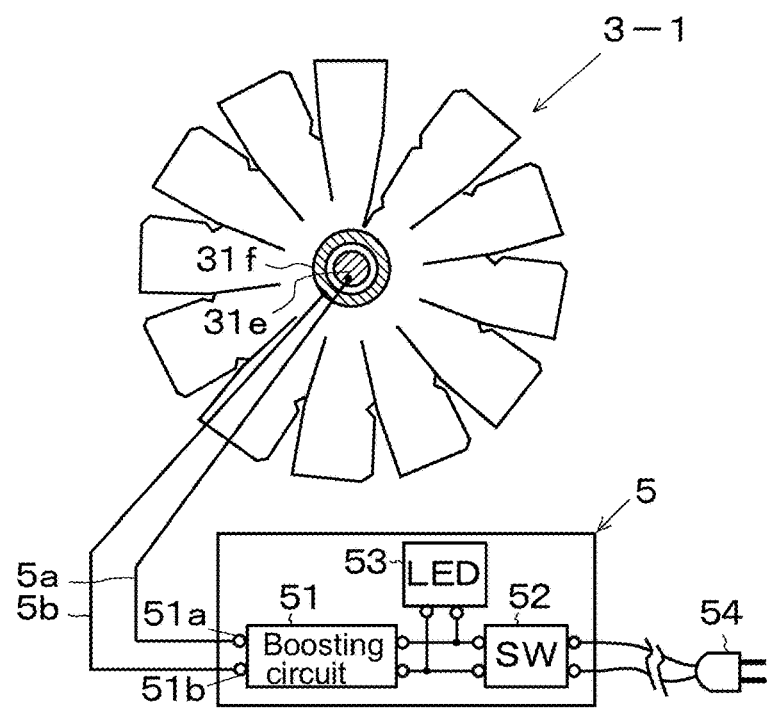
FIG. 6 is an electrical wiring diagram showing the connection between a terminal on the inner side surface of the developed ozone generator body and the voltage supply part.

FIG. 5 is an electrical wiring diagram showing the connection between the cross-sectionally shown ozone generator body and the voltage supply part and FIG. 6 is an electrical wiring diagram showing the connection between terminals on the inner side surface of the developed ozone generator body and the voltage supply part.

The voltage supply part 5 shown in FIG. 1, which is provided to supply a voltage required to generate ozone to the ozone generator 2, is connected electrically to terminals 31e, 31f provided in a central portion on the inner surface of the ozone generator body 3-1, as shown in FIGS. 5 and 6.

In particular, as shown in FIG. 1, a boosting circuit 51 is housed within a case body 50 of the voltage supply part 5, and a switch 52 and an LED lamp 53 are attached to the top surface of the case body 50.

The power supply for the thus arranged voltage supply part 5 is an AC commercial power supply, and a plug 54 for the AC commercial power supply is connected electrically to an input terminal of the boosting circuit 51 via the switch 52, as shown in FIGS. 5 and 6. The LED lamp 53 is then connected between the boosting circuit 51 and the switch 52.

One output terminal 51a of the boosting circuit 51 is connected through a wire 5a to the single circular terminal 31e provided in the central portion on the inner surface of the ozone generator body 3-1, while another output terminal 51b is connected through a wire 5b to the ring-shaped terminal 31f provided on the outside of the terminal 31e.

Meanwhile, as shown in FIG. 5, the terminal 31c positioned at the center within the ozone generator body 3-1 is connected through a via hole to the circular terminal 31e, while all of the twelve terminals 31d around the terminal 31c are connected through via holes to the ring-shaped terminal 31f. In turn, as shown in FIGS. 3 and 4, all of the twelve electrodes 31a are connected to the terminal 31c, while the twelve electrodes 31b are connected, respectively, to the twelve terminals 31d. Accordingly, the output terminal 51a of the voltage supply part 5 is connected electrically to all of the twelve electrodes 31a through the wire 5a and the terminals 31e, 31c, while the output terminal 51b is connected electrically to all of the twelve electrodes 31b through the wire 5b and the terminals 31f, 31d. That is, the twelve pairs of electrodes 31a, 31b are connected in parallel to the voltage supply part 5.

This allows the boosting circuit 51 of the voltage supply part 5, when the switch 52 is turned on, to boost an AC commercial voltage input through the plug 54 up to a voltage required to generate ozone and supply it to the twelve respective pairs of electrodes 31a, 31b of the ozone generator body 3-1.

Next will be described an example of how the headgear cleaner of this embodiment is used.

Figure 7:
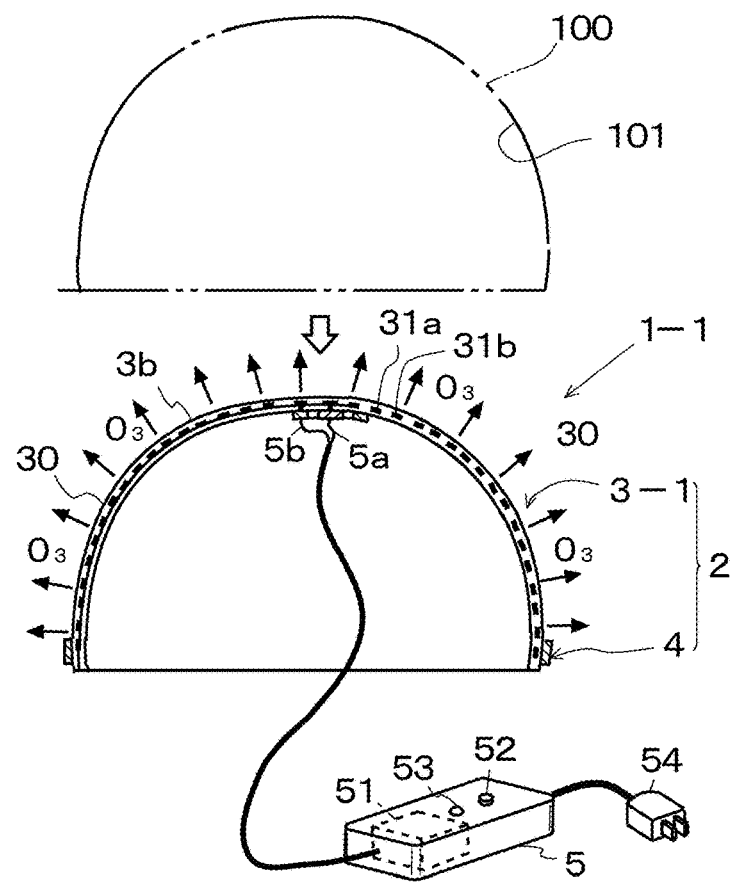
FIG. 7 is a schematic cross-sectional view for illustrating operations and effects of the embodiment.

FIG. 7 is a schematic cross-sectional view for illustrating operations and effects of the embodiment.

In FIG. 7, when a helmet 100 indicated by the alternate long and two short dashed line is sterilized and deodorized, first, the helmet 100 is put on the ozone generator 2 of the headgear cleaner 1-1 or the headgear cleaner 1-1 is put inside of the helmet 100.

At this time, if, like the ozone generator 2, the inner surface 101 of the helmet 100 has a semispherical shape, the ozone generator 2 fits exactly inside of the helmet 100.

However, if the interior of the helmet 100 does not have a semispherical shape, it may not be put on the ozone generator 2. Even in such a case where the shape of the helmet 100 is different from the shape of the ozone generator 2, the ozone generator 2, which is formed of flexible material as described above, is deformed to follow the shape of the inner surface 101 of the helmet 100. As a result, the ozone generator 2 fits exactly inside of the helmet 100.

Next, when the plug 54 is inserted into an outlet jack of the AC commercial power supply not shown and the switch 52 of the voltage supply part 5 is turned on, the LED lamp 53 is turned on and the voltage supply part 5 is activated, so that a predetermined voltage is supplied from the boosting circuit 51 through the wires 5a, 5b to the twelve pairs of electrodes 31a, 31b of the ozone generator 2. This causes discharge between each pair of electrodes 31a, 31b and thereby ozone $O_3$ is released peripherally from the surface 3b of the ozone generator body 3-1 of the ozone generator 2.

In addition, since the surface 3b of the ozone generator body 3-1 is in close proximity to the inner surface 101 of the helmet 100, ozone $O_3$ released from the ozone generator body 3-1 reliably sterilizes and deodorizes the entire inner surface 101 of the helmet 100.

Further, since the dielectric 32 of the ozone generator body 3-1 is formed of polymeric resin having a permittivity equal to or higher than 3 and a dielectric breakdown voltage equal to or higher than 15 kV/mm, the ozone generator body 3-1 can withstand high voltage and easily generate plasma for ozone $O_3$ generation.

On the other hand, if it is desired to sterilize and deodorize not a three-dimensional object like the helmet 100 but a two-dimensional object, the connecting part 4 is detached from the ozone generator body 3-1 to develop the ozone generator body 3-1 into a planar shape, as shown in FIG. 2. In this state, the two-dimensional object can be, for example, placed on the developed ozone generator body 3-1 for sterilization and deodorization.

When the sterilizing and deodorizing operation by the headgear cleaner 1-1 is finished, the switch 52 of the voltage supply part 5 shown in FIG. 7 is turned off. This causes the AC voltage input from the outlet jack to be cut off and the LED lamp 53 to be turned off.

After use, the headgear cleaner 1-1 can be stored in a storage area with the voltage supply part 5 with the ozone generator 2 having a three-dimensional shape. However, if the storage area is small, the ozone generator body 3-1 of the ozone generator 2 may be developed into a planar shape, as shown in FIG. 2, to store the headgear cleaner 1-1 easily even in such a small storage area.

Figure 8:
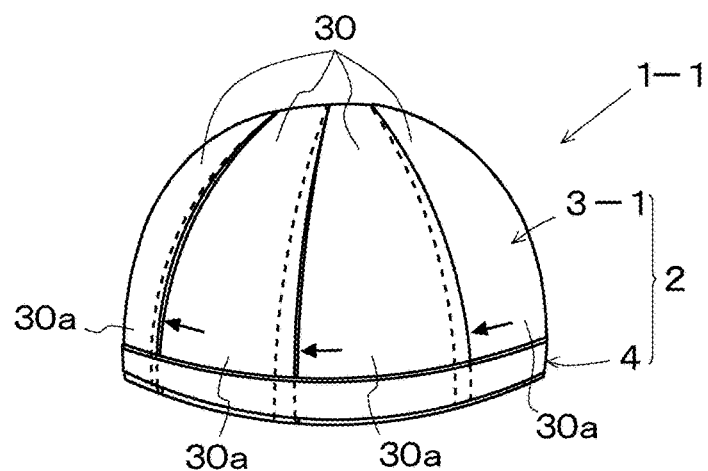
FIG. 8 is a perspective view for illustrating a size adjustment function of an ozone generator.

FIG. 8 is a perspective view for illustrating a size adjustment function of an ozone generator.

If it is desired to pre-adjust the size of the ozone generator 2, the lower end portions 30a of the leaf parts 30 of the ozone generator body 3-1 are shifted in the lateral direction of the ozone generator body 3-1, as shown by the arrows in FIG. 8, to bring adjacent ones of the leaf parts 30 close to each other. This allows the ozone generator body 3-1 to have a reduced diameter. On the contrary, the lower end portions 30a of the leaf parts 30 may be shifted in the direction opposite to that indicated by the arrows in FIG. 8 to steer adjacent ones of the leaf parts 30 away from each other so that the ozone generator body 3-1 has an increased diameter.

That is, in the headgear cleaner 1-1 of this embodiment, the size of the ozone generator 2 can be adjusted for application to helmets 100 of various sizes.

(First Variation)

Figure 9:
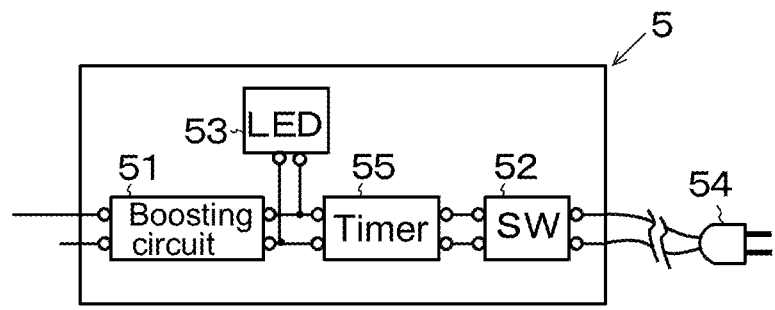
FIG. 9 is a circuit block diagram showing a voltage supply part as a substantial part of a first variation of the first embodiment.

FIG. 9 is a circuit block diagram showing a voltage supply part as a substantial part of a first variation of the first embodiment.

As shown in FIG. 9, this variation includes a timer 55 provided within the voltage supply part 5.

Specifically, the timer 55 is interposed between the switch 52 and the boosting circuit 51.

Thus, when the switch 52 is turned on, the timer 55 and the boosting circuit 51 are activated. When a drive time (e.g. two hours) set in the timer 55 has elapsed, the timer 55 automatically shuts down the boosting circuit 51.

(Second Variation)

Figure 10:
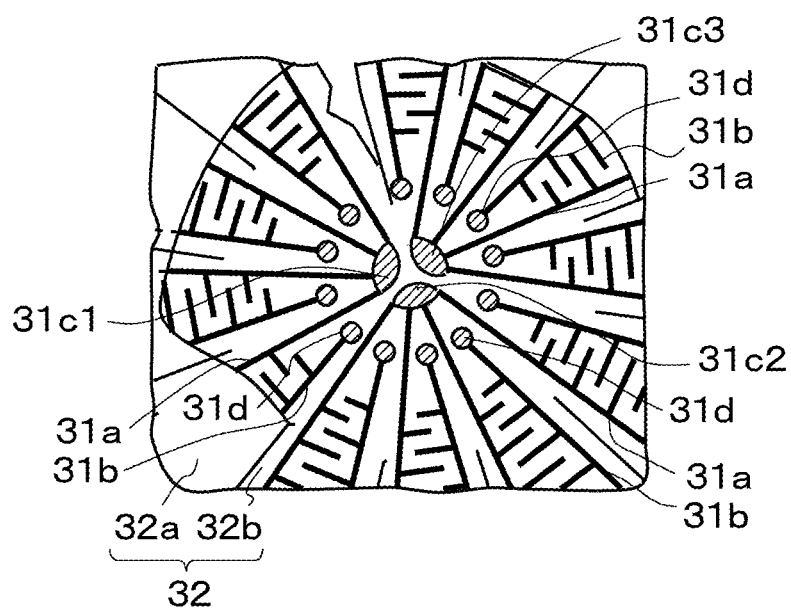
FIG. 10 is a partially-cutaway partially-enlarged view showing an ozone generator body as a substantial part of a second variation of the first embodiment.
Figure 11:
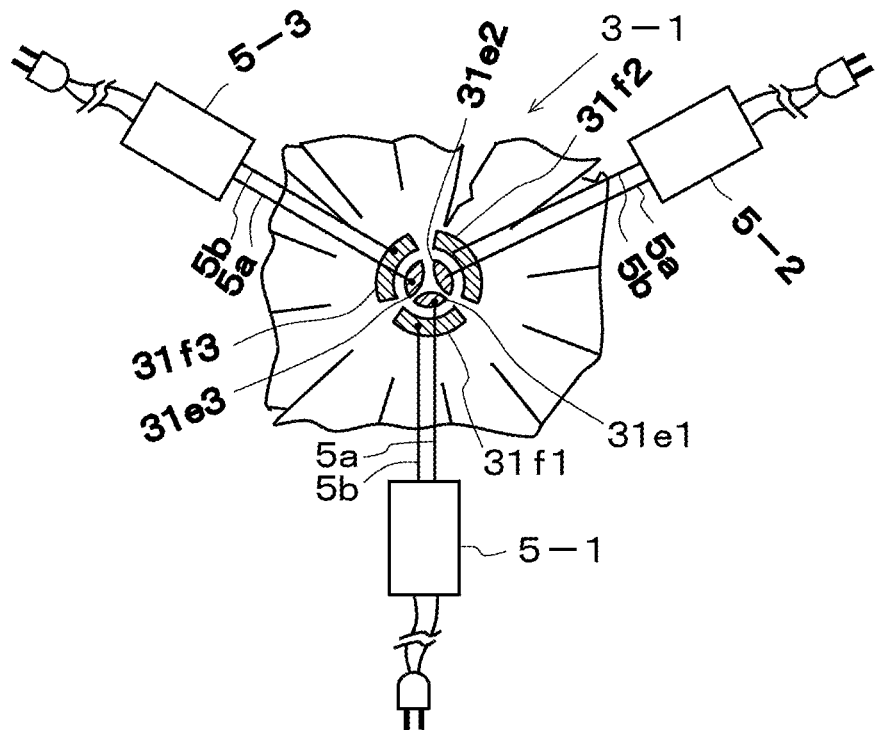
FIG. 11 is a partially-enlarged view showing the inner side surface of the ozone generator body as a substantial part of the second variation.

FIG. 10 is a partially-cutaway partially-enlarged view showing the ozone generator body as a substantial part of a second variation of the first embodiment and FIG. 11 is a partially-enlarged view showing the inner side surface of the ozone generator body as a substantial part of the second variation.

While in the above-described first embodiment, the twelve pairs of electrodes 31a, 31b are connected in parallel to the single voltage supply part 5, as shown in FIGS. 3 and 4, the twelve pairs of electrodes 31a, 31b may be connected in a distributed manner to multiple voltage supply parts 5 to supply a stabilized voltage to each pair of electrodes 31a, 31b.

For example, as shown in FIG. 10, the twelve electrodes 31b are connected, respectively, to twelve terminals 31d, while every four of the electrodes 31a are connected, respectively, to three terminals 31c1 to 31c3.

As shown in FIG. 11, the three terminals 31c1 to 31c3 are then connected, respectively, through via holes to three terminals 31e1 to 31e3 provided on the inside of the ozone generator body 3-1. Every four of the terminals 31d are connected, respectively, through via holes to three arc-shaped terminals 31f1 to 31f3. Then, the voltage supply part 5-1 is connected through the wires 5a, 5b to the terminals 31e1, 31f1, the voltage supply part 5-2 is connected through the wires 5a, 5b to the terminals 31e2, 31f2, and the voltage supply part 5-3 is connected through the wires 5a, 5b to the terminals 31e3, 31f3.

(Third Variation)

Figure 12:
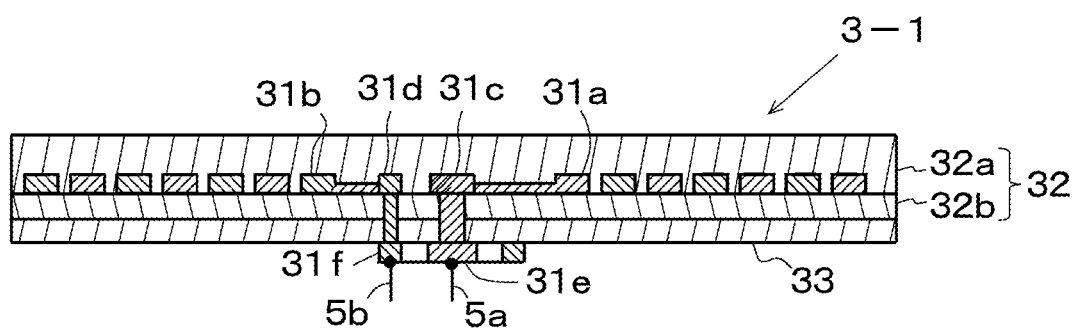
FIG. 12 is a schematic cross-sectional view showing a substantial part of a third variation of the first embodiment.

FIG. 12 is a schematic cross-sectional view showing a substantial part of a third variation of the first embodiment.

While in the above-described first embodiment, the ozone generator body 3-1 of the ozone generator 2 is formed only with the electrodes 31a, 31b and the dielectric 32, as shown in FIG. 5, a flexible and rigid base material 33 may be attached to the side under the dielectric 32 to increase the entire strength of the ozone generator body 3-1. As a result, the helmet 100, when being put on the ozone generator 2, is stabilized on the ozone generator 2.

Second Embodiment

Next will be described a second embodiment of the present invention.

Figure 13:
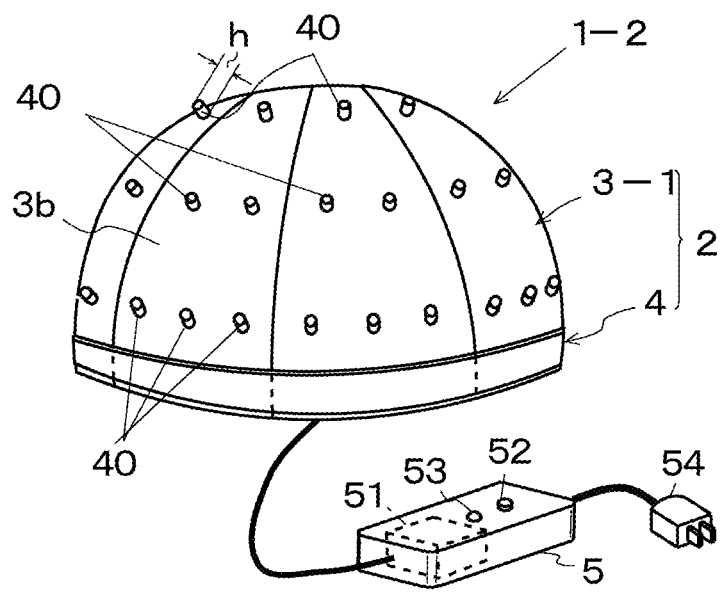
FIG. 13 is a perspective view showing a headgear cleaner according to a second embodiment of the present invention.
Figure 14:
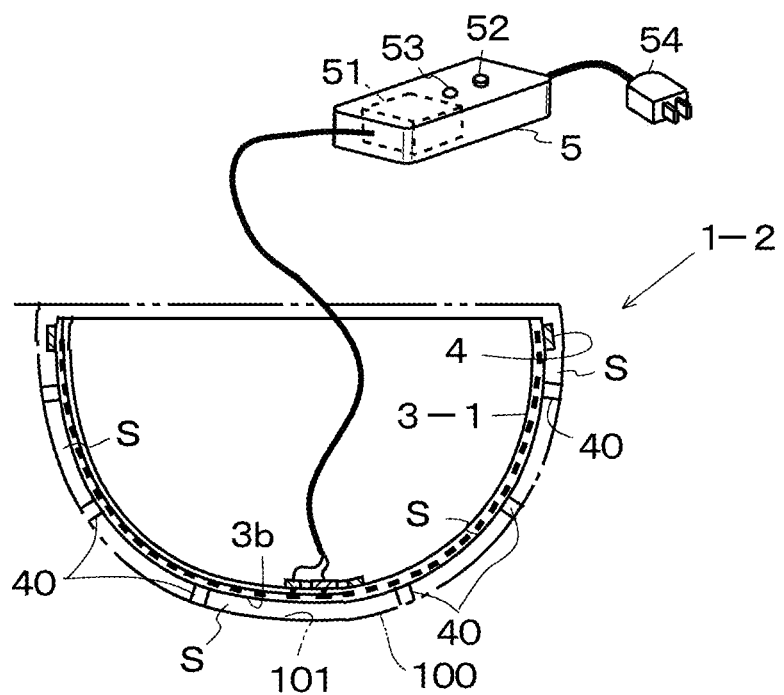
FIG. 14 is a schematic cross-sectional view for illustrating sterilizing and deodorizing effects.

FIG. 13 is a perspective view showing a headgear cleaner according to the second embodiment of the present invention and FIG. 14 is a schematic cross-sectional view for illustrating sterilizing and deodorizing effects.

The headgear cleaner 1-2 of this embodiment is different from that of the above-described first embodiment in that multiple spacers 40 are provided in a manner protruding from the surface 3b of the ozone generator body 3-1 of the ozone generator 2.

Specifically, as shown in FIG. 13, multiple spacers 40 having a height h equal to or smaller than 10 mm are disposed in a distributed manner on the surface 3b of the ozone generator body 3-1.

Thus, as shown in FIG. 14, when the ozone generator 2 of the headgear cleaner 1-2 is put inside of the helmet 100 indicated by the alternate long and two short dashed line, the spacers 40 provide a gap S between the surface 3b of the ozone generator body 3-1 and the inner surface 101 of the helmet 100. As a result, a large amount of air is introduced externally into the gap S to accelerate ozone generation by the ozone generator body 3-1.

Meanwhile, upon sterilization and deodorization by the headgear cleaner 1-2 with the helmet 100 put thereon, if the inner surface 101 of the helmet 100 is smooth, bacteria on the inner surface 101 can be sterilized and deodorized almost completely by ozone regardless of the distance between the surface 3b of the ozone generator body 3-1 and the inner surface 101 of the helmet 100.

However, if the inner surface 101 of the helmet 100 is rough or a rough material, cloth, or artificial leather is attached to the inner surface 101, an increased distance between the inner surface 101 and the surface 3b of the ozone generator body 3-1 can provide less sterilizing effects.

Hence, in this embodiment, the height h of the spacers 40 is set within the range equal to or smaller than 10 mm to position the rough inner surface 101 of the helmet 100 to be sterilized in the vicinity of the surface 3b of the ozone generator body 3-1.

This causes ozone and radicals, etc., generated from the surface 3b of the ozone generator body 3-1 to effectively come into contact with the inner surface 101 of the helmet 100, and high sterilization and deodorization effects are obtained.

The inventors have conducted the following experiment to demonstrate the above-described effects.

FIG. 15 are transferred images of photographs showing survival states of bacteria.

The inventors have conducted this experiment in a general indoor environment.

First, as preparation, bacteria (common bacteria, hereinafter, referred to as "bacteria K") were separately cultured, and the bacteria K were sprayed onto a polyester cotton blend cloth piece not shown in the drawings, and then the cloth piece was dried.

Figure 15A:
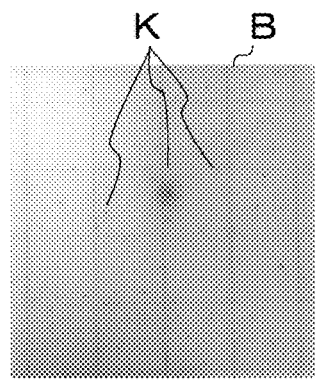
FIGS. 15(*a*) to 15(*f*) are transferred images of photographs showing survival states of bacteria.

Then, the surface of the thus prepared cloth piece was wiped with a 5 cm-square culture medium B, and the bacteria K were cultured in this culture medium B for 48 hours at a temperature of 35° C. Then, as shown in FIG. 15(*a*), "137" bacteria K survived in the 5 cm-square culture medium B.

That is, it was confirmed that, in the state where ozone treatment was not applied, the number of surviving bacteria K was "137."

Next, the prepared cloth piece was fixed xmm just below an electrode sheet (not shown) having the same structure as each leaf part 30 of the ozone generator body 3-1 with the surface on which the bacteria K were sprayed facing the electrode sheet. In this state, ozone was generated from the electrode sheet and the cloth piece was exposed to ozone for two hours. At this time, the ozone was generated by supplying a pulsed power of 14 kV p-p at a frequency of 13 Hz to the electrode sheet.

Thereafter, the surface of the cloth piece to which ozone treatment was applied was wiped with a 5 cm-square culture medium B, and the bacteria K were cultured in this culture medium B for 48 hours at a temperature of 35° C.

Figure 15B:
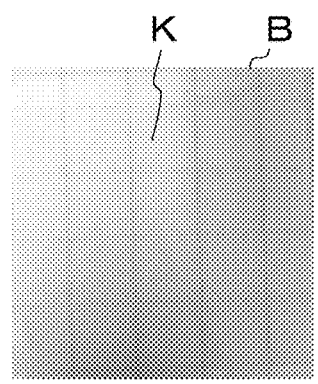
Figure 15C:
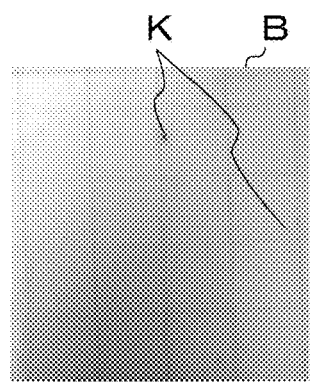
Figure 15D:
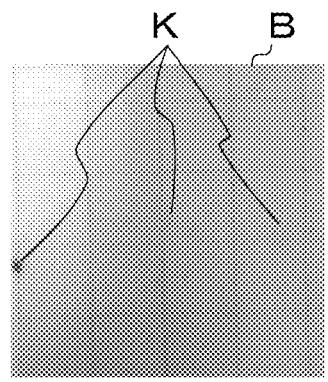
Figure 15E:
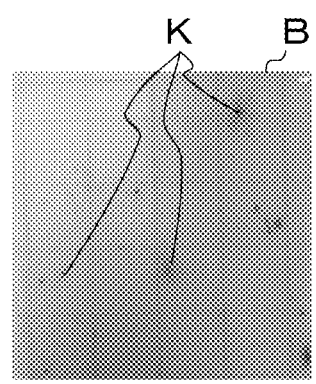
Figure 15F:
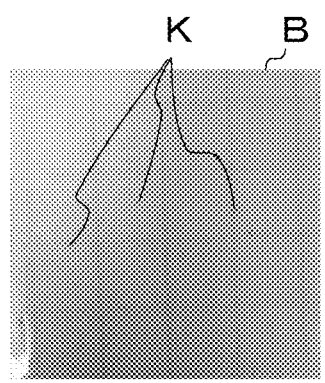

The ozone treatment described above was applied by setting the distance xmm between the cloth piece and the electrode sheet to 2 mm, 5 mm, 10 mm, 20 mm, and 30 mm. Then, when the distance between the cloth piece and the electrode sheet was 2 mm, as shown in FIG. 15(*b*), the number of surviving bacteria K in the 5 cm-square culture B was "1," and when the distance between the cloth piece and the electrode sheet was 5 mm, as shown in FIG. 15(*c*), the number of surviving bacteria K in the 5 cm-square culture B was "19," and when the distance between the cloth piece and the electrode sheet was 10 mm, as shown in FIG. 15(*d*), the number of surviving bacteria K in the 5 cm-square culture B was "51," and when the distance between the cloth piece and the electrode sheet was 20 mm, as shown in FIG. 15(*e*), the number of surviving bacteria K in the 5 cm-square culture B was "103," and when the distance between the cloth piece and the electrode sheet was 30 mm, as shown in FIG. 15(*f*), the number of surviving bacteria K in the 5 cm-square culture B was "102."

That is, it was confirmed that in the state where ozone treatment was applied, when the distance between the cloth piece and the electrode sheet was increased, the number of surviving bacteria K increased.

Figure 16:
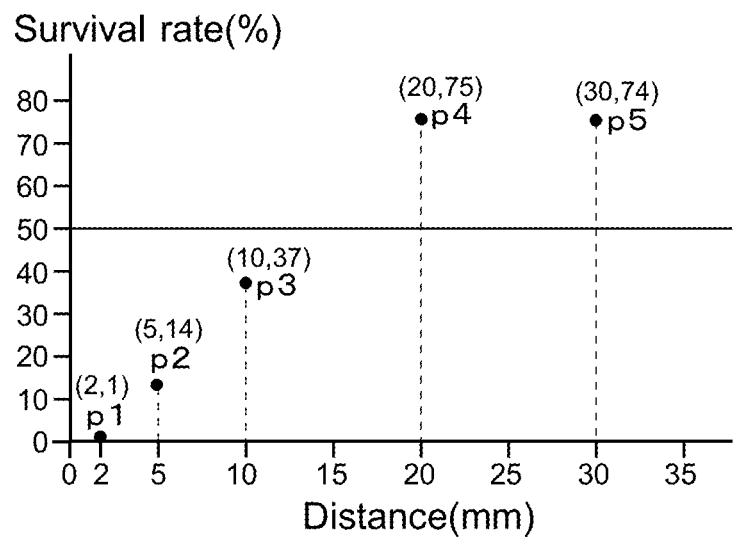
FIG. 16 is a graph showing the relationship between the survival rate of bacteria and the distance.
Figure 17:
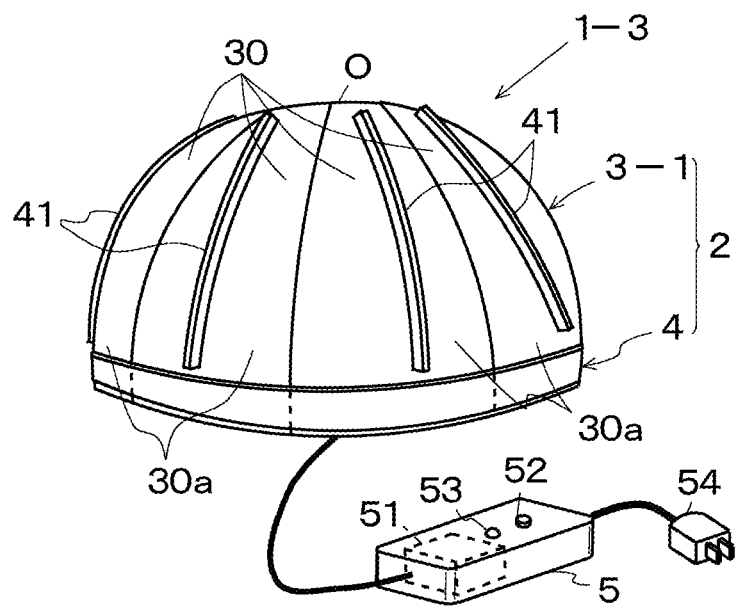
FIG. 17 is a perspective view showing a headgear cleaner according to a third embodiment of the present invention.
Figure 18:
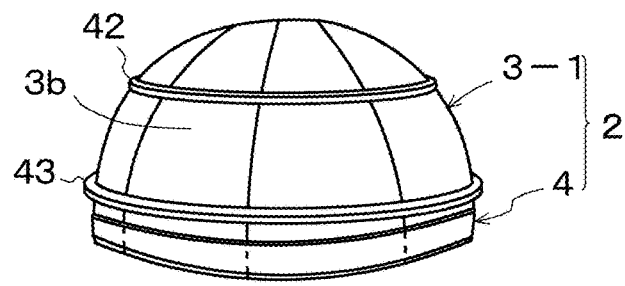
FIG. 18 is a perspective view showing a first variation of the third embodiment.
Figure 19:
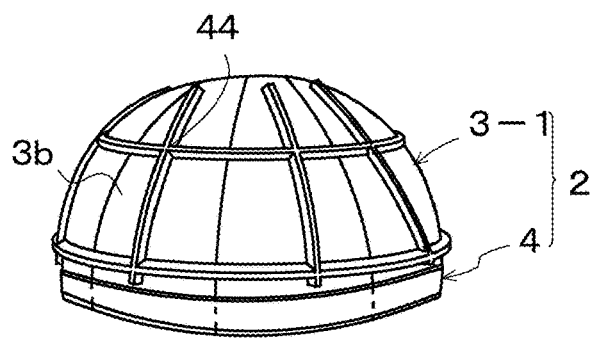
FIG. 19 is a perspective view showing a second variation of the third embodiment.

FIG. 16 is a graph showing the relationship between the survival rate of bacteria K and the distance.

The inventors defined the survival rate of bacteria K as (number of bacteria after ozone treatment/number of bacteria before ozone treatment)×100(%) and plotted the relationship between the distance between the electrode sheet and the cloth piece and the survival rate of bacteria K in the ozone treatment described above.

As a result, points p1 to p5 were obtained, as shown in FIG. 16.

As shown by the points p1, p2, p3, when the distance was set to 2 mm, 5 mm, 10 mm, the survival rate was 1%, 14%, 37%, and these are lower than a reference survival rate of 50%.

On the other hand, as shown by the points p4, p5, when the distance was set to 20 mm, 30 mm, the survival rate was 75%, 74%, and these are much higher than the reference survival rate of 50%.

Based on the experimental results above, it can be determined that the distance between the cloth piece and the electrode sheet to reliably reduce the survival rate to be less than 50% is 10 mm or less.

Therefore, the inventors have set the distance h to be kept by the spacers 40 shown in FIGS. 13 and 14 within the range equal to or smaller than 10 mm. That is, keeping the distance h between the inner surface 101 of the helmet 100 and the surface 3*b* of the ozone generator body 3-1 within the range equal to or smaller than 10 mm allows the survival rate of bacteria K on the inner surface 101 of the helmet 100 to be kept below the reference survival rate of 50%, as shown in FIG. 16.

Figure 20:
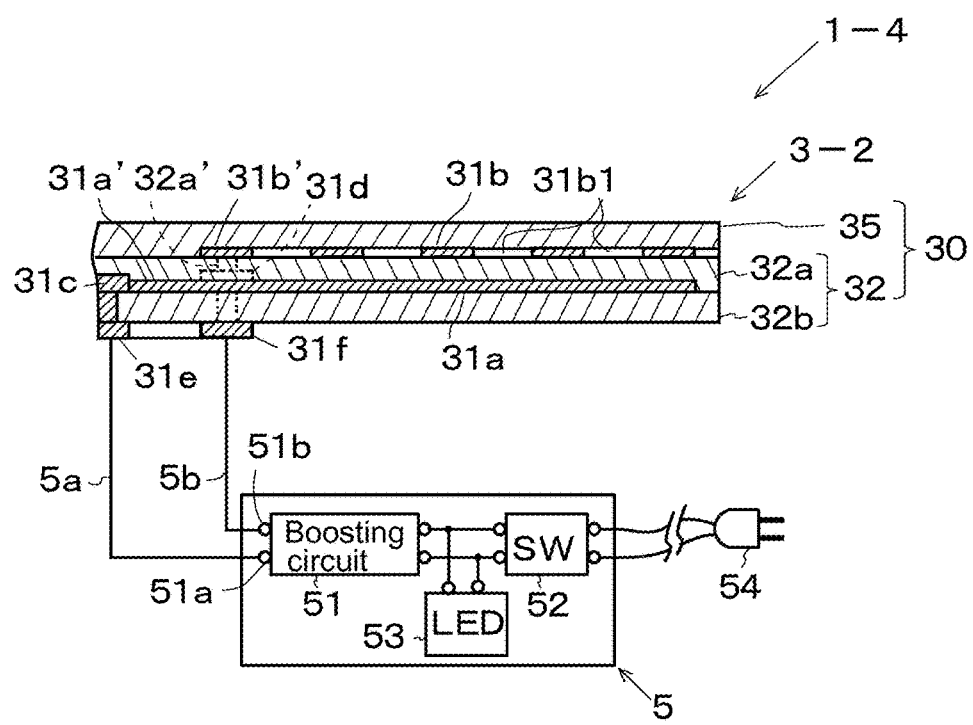
FIG. 20 is a schematic cross-sectional view showing a substantial part of a headgear cleaner according to a fourth embodiment of the present invention.
Figure 21:
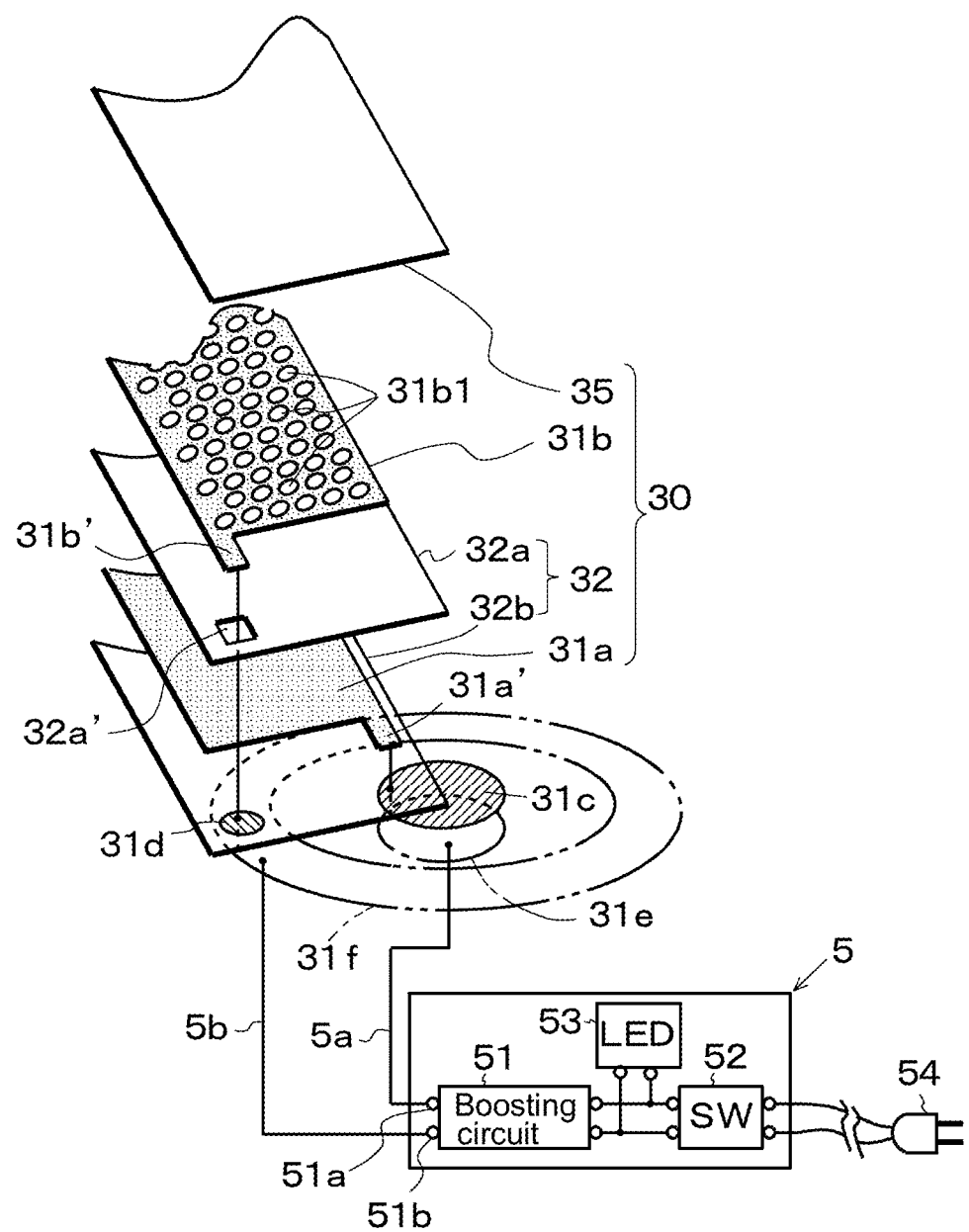
FIG. 21 is an exploded perspective view showing the substantial part of FIG. 20.

Since the other configurations, operations, and effects are the same as those in the above-described first embodiment, the description thereof will be omitted.

Third Embodiment

Next will be described a third embodiment of the present invention.

FIG. 17 is a perspective view showing a headgear cleaner according to the third embodiment of the present invention.

As shown in FIG. 17, this embodiment is different from the above-described second embodiment in that the spacers each have not a protruding shape but a linear body.

Specifically, the spacers 41 are linear bodies set to have a height equal to or smaller than 10 mm and attached one by one to each leaf part 30 of the ozone generator body 3-1. In particular, each spacer 41 is attached to each leaf part 30 in a manner running from the top portion O of the ozone generator body 3-1 to the lower end portion 30*a* of the leaf part 30.

Since the other configurations, operations, and effects are the same as those in the above-described first and second embodiments, the description thereof will be omitted.

(Fourth Variation)

FIG. 18 is a perspective view showing a first variation of the third embodiment.

As shown in FIG. 18, ring-shaped spacers 42, 43 having their respective different diameters are fitted on the surface 3*b* of the ozone generator body 3-1. These spacers 42, 43 are also set to have a height equal to or smaller than 10 mm.

(Fifth Variation)

FIG. 19 is a perspective view showing a second variation of the third embodiment.

As shown in FIG. 19, a lattice-shaped spacer 44 is put on the surface 3*b* of the ozone generator body 3-1. This spacer 44 is also set to have a height equal to or smaller than 10 mm.

It is noted that while the lattice-shaped spacer 44 is here exemplified as a spacer, not only such a lattice-shaped one but also a plate body having a number of holes or a mesh body formed by thin wires can be applied as a spacer.

Fourth Embodiment

Next will be described a fourth embodiment of the present invention.

FIG. 20 is a schematic cross-sectional view showing a substantial part of a headgear cleaner according to the fourth embodiment of the present invention and FIG. 21 is an exploded perspective view showing the substantial part of FIG. 20.

It is noted that FIGS. 20 and 21 show one leaf part 30 of an ozone generator body 3-2.

As shown in FIG. 20, in the headgear cleaner 1-4 of this embodiment, the structure of the ozone generator body 3-2 is different from those of the ozone generator bodies 3-1 in the above-described embodiments.

That is, in each pair of electrodes 31a, 31b, only the electrode 31a is housed in the dielectric 32, while the electrode 31b is provided on the surface of the dielectric 32.

Specifically, as shown in FIG. 21, a solid electrode 31a is formed and laminated on a lower dielectric layer 32b, on which an upper dielectric layer 32a is laminated to cover the electrode 31a. An electrode 31b having approximately the same shape as the electrode 31a is then formed on the dielectric layer 32a. A protective layer 35 is further laminated on the electrode 31b.

Also, a terminal portion 31a' is provided in a leading end portion of the electrode 31a and connected to a terminal 31c on the dielectric layer 32b.

On the other hand, a terminal portion 31b' is provided in a leading end portion of the electrode 31b and connected through a via hole 32a' in the dielectric layer 32a to a terminal 31d on the dielectric layer 32b. In the thus arranged electrode 31b, a number of circular holes 31b1 are bored at regular intervals.

As is the case with the ozone generator bodies 3-1 of the above-described first to third embodiments, the ozone generator body 3-2 of this embodiment is also entirely formed of polymeric resin. That is, not only are the dielectric layers 32a, 32b and the protective layer 35 each formed of polyimide resin, but also the electrodes 31a, 31b are formed of conductive polymer, a kind of polymeric resin.

In this embodiment, the protective layer 35 is provided on the electrode 31b that is on the surface of the dielectric 32. However, the protective layer 35 is not an essential member, and may not be provided in some cases.

Since the other configurations, operations, and effects are the same as those in the above-described first to third embodiments, the description thereof will be omitted.

(Sixth Variation)

Figure 22A:
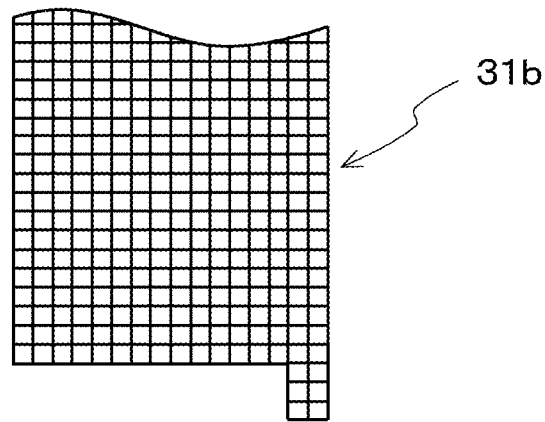
FIGS. 22(*a*) and 22(*b*) are plan views showing variations of an electrode applied in the fourth embodiment, where FIG. 22(*a*) shows a first variation of the fourth embodiment and FIG. 22(*b*) shows a second variation of the fourth embodiment.
Figure 22B:
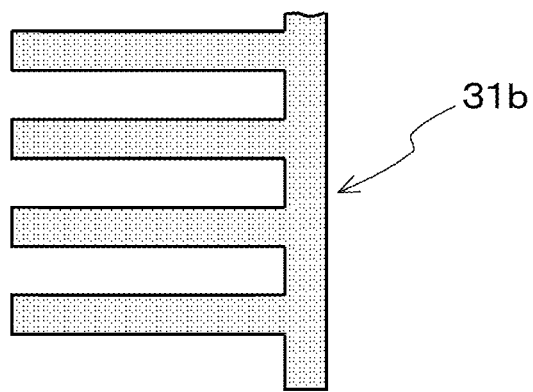

FIGS. 22(a) and 22(b) are plan views showing variations of an electrode applied in the fourth embodiment, where FIG. 22(a) shows a first variation of the fourth embodiment and FIG. 22(b) shows a second variation of the fourth embodiment.

While in the above-described fourth embodiment, the electrode 31b having a number of circular holes 31b1 is applied as the other electrode as shown in FIG. 21, a mesh electrode 31b may be applied as the other electrode as shown in FIG. 22(a). Alternatively, a comb-shaped electrode 31b may be applied as the other electrode as shown in FIG. 22(b).

Fifth Embodiment

Next will be described a fifth embodiment of the present invention.

Figure 23:
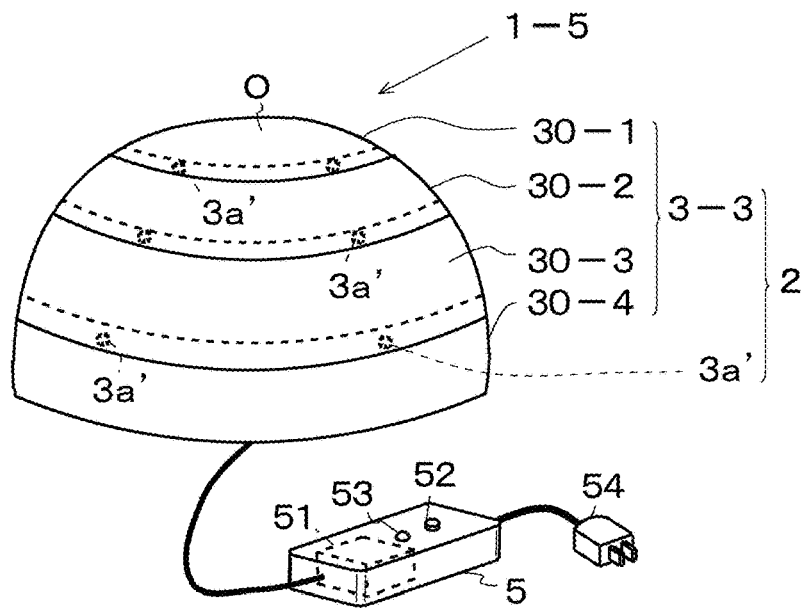
FIG. 23 is a perspective view showing a headgear cleaner according to a fifth embodiment of the present invention.
Figure 24:
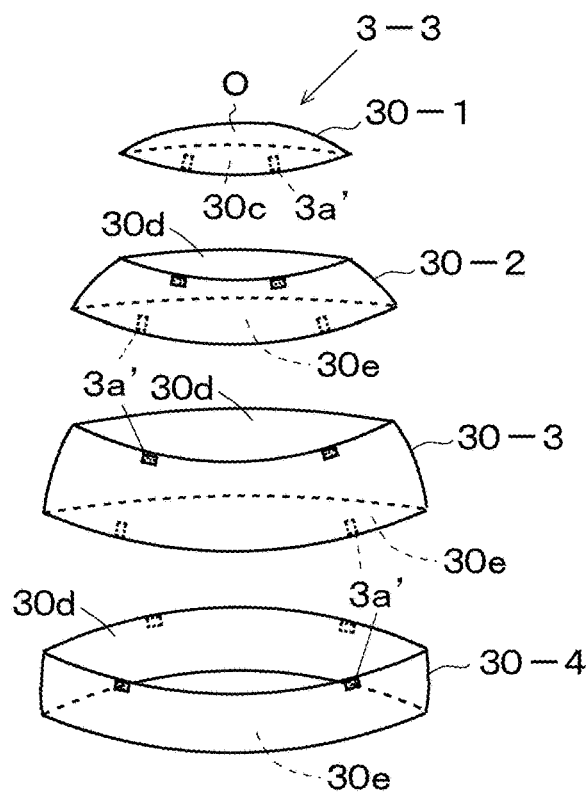
FIG. 24 is an exploded perspective view showing an ozone generator.

FIG. 23 is a perspective view showing a headgear cleaner according to the fifth embodiment of the present invention and FIG. 24 is an exploded perspective view showing an ozone generator.

As shown in FIG. 23, in the headgear cleaner 1-5 of this embodiment, the ozone generator body 3-3 is formed by one top part 30-1, three annular parts 30-2 to 30-4, and multiple Velcro tape pieces 3a' as a connecting part.

Specifically, as shown in FIG. 24, the three annular parts 30-2 to 30-4, having their respective different diameters, are disposed in this order below the single top part 30-1. The top part 30-1 and the three annular parts 30-2 to 30-4 are then assembled into an approximately semispherical hull shape to form the ozone generator body 3-3. The shape of the ozone generator body 3-3 is kept by the Velcro tape pieces 3a'.

More particularly, in each annular part 30-2 (30-3, 30-4), the lower opening portion 30e is set to have a size larger than that of the upper opening portion 30d. The lower opening portion 30e of an upper one 30-2 (30-3, 30-4) of the annular parts is then set to have a size approximately equal to that of the upper opening portion 30d of the directly underlaid annular part 30-3 (30-4). In addition, the opening 30c of the top part 30-1 is set to have a size approximately equal to that of the upper opening portion 30d of the annular part 30-2.

The top part 30-1 and the three annular parts 30-2 to 30-4 are then disposed in series downward from the top portion O with the opening 30c of the top part 30-1 fitted on the upper opening portion 30d of the annular part 30-2, the lower opening portion 30e of the annular part 30-2 fitted on the upper opening portion 30d of the annular part 30-3, and the lower opening portion 30e of the annular part 30-3 fitted on the upper opening portion 30d of the annular part 30-4.

In addition, the Velcro tape piece 3a' provided in a lower portion on the interior surface of the top part 30-1 and the Velcro tape piece 3a' provided in an upper portion on the exterior surface of the annular part 30-2 are fastened to each other, the Velcro tape piece 3a' provided in a lower portion on the interior surface of the annular 30-2 and the Velcro tape piece 3a' provided in an upper portion on the exterior surface of the annular part 30-3 are fastened to each other, and the Velcro tape piece 3a' provided in a lower portion on the interior surface of the annular 30-3 and the Velcro tape piece 3a' provided in an upper portion on the exterior surface of the annular part 30-4 are fastened to each other to thereby keep the entire ozone generator body 3-3 in an approximately semispherical hull shape.

It is noted that in this embodiment, each annular part 30-2 (30-3, 30-4) is structured to cover one pair of electrodes 31a, 31b with the dielectric 32, though not shown, and the three pairs of electrodes 31a, 31b disposed in the three respective annular parts 30-2 to 30-4 are connected in parallel to the voltage supply part 5.

With the arrangement above, a user can put a helmet 100 (see FIG. 1) on the ozone generator 2 that is formed by the ozone generator body 3-3 and the Velcro tape pieces 3a' or can put the ozone generator 2 inside of the helmet 100.

At this time, in the arrangement above, an upper one 30-2 (30-3) of the annular parts and the directly underlaid annular part 30-3 (30-4) may be moved up and down and the Velcro tape pieces 3a' may be fastened to each other to freely adjust the depth of the ozone generator body 3-3, that is, the depth of the ozone generator 2.

Since the other configurations, operations, and effects are the same as those in the above-described first to fourth embodiments, the description thereof will be omitted.

Sixth Embodiment

Next will be described a sixth embodiment of the present invention.

Figure 25:
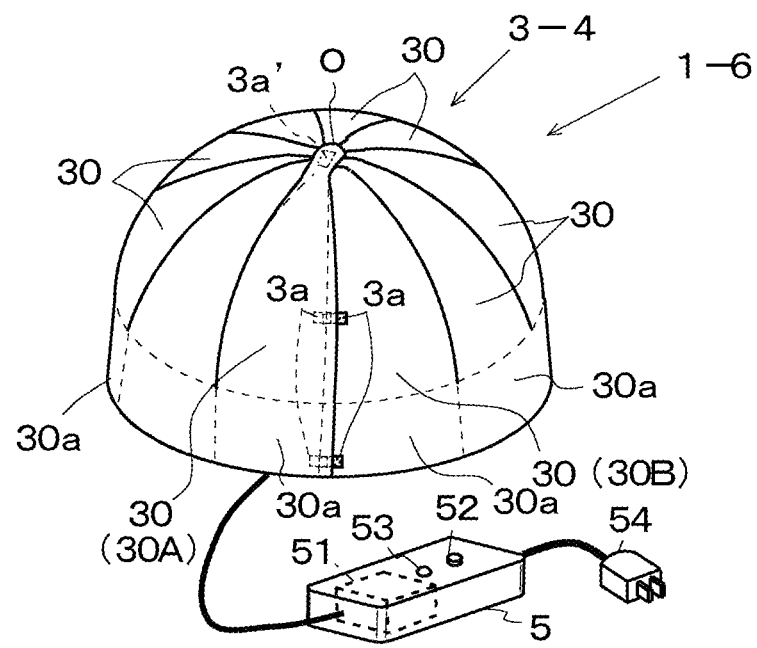
FIG. 25 is a perspective view showing a headgear cleaner according to a sixth embodiment of the present invention.
Figure 26:
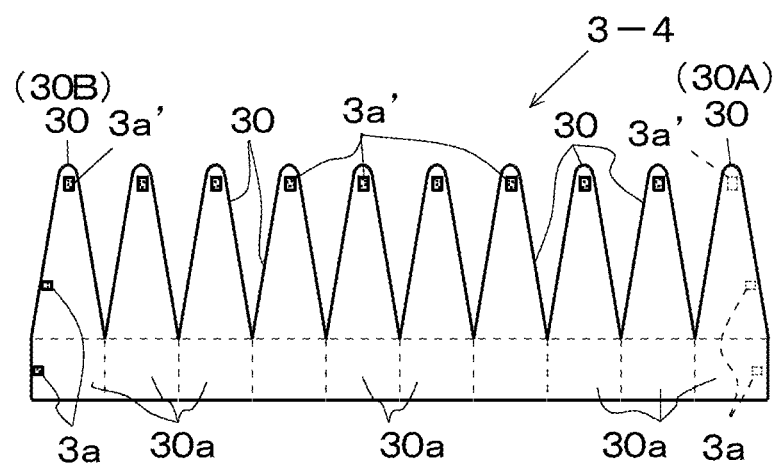
FIG. 26 is a developed view showing an ozone generator.

FIG. 25 is a perspective view showing a headgear cleaner according to the sixth embodiment of the present invention and FIG. 26 is a developed view showing an ozone generator.

The headgear cleaner 1-6 of this embodiment is similar to the headgear cleaner 1-1 of the above-described first embodiment in that the ozone generator body 3-4 is formed by multiple leaf parts 30 as shown in FIG. 25, but different from that of the above-described first embodiment in that the developed shape of the ozone generator body 3-4 is similar to the upper half of the shape obtained by developing a terrestrial globe with a boat-shaped polyconical projection as shown in FIG. 26.

As shown in FIG. 25, the lower end portions 30a of ten leaf parts 30 are connected circularly. In the state where the lower end portions 30a are thus connected, the ozone generator body 3-4 is structured such that the upper end portion sides of the ten leaf parts 30 are curved upward. The multiple Velcro tape pieces 3a, 3a' as a connecting part then keep the overall shape of the ten leaf parts 30 in an approximately semispherical hull shape.

Specifically, as shown in FIG. 26, Velcro tape pieces 3a are provided on the right end leaf part 30 (hereinafter referred to as "leaf part 30A"), respectively, in a lower end portion 30a and a central portion on the interior surface of the leaf part 30, while a Velcro tape piece 3a' is provided in an upper end portion on the interior surface of the leaf part 30A. On the other hand, Velcro tape pieces 3a are provided on the left end leaf part 30 (hereinafter referred to as "leaf part 30B"), respectively, in a lower end portion 30a and a central portion on the exterior surface of the leaf part 30B, while Velcro tape pieces 3a' are provided, respectively, in an upper end portion on the exterior surface and in an upper end portion on the interior surface of the leaf part 30B. Then, Velcro tape pieces 3a' are provided, respectively, in an upper end portion on the exterior surface and in an upper end portion on the interior surface of each of the eight leaf parts 30 that are positioned between the lead part 30A and the leaf part 30B.

In the structure above, the Velcro tape pieces 3a on the leaf part 30A and the corresponding Velcro tape pieces 3a on the leaf part 30B are fastened to each other to connect the adjacent leaf parts 30A and 30B. The upper end portion sides of all the leaf parts 30 including the leaf part 30A and the leaf part 30B are then curved toward the top portion O, as shown in FIG. 25, and connected by the Velcro tape pieces 3a' in a manner collected at the top portion O with the upper end portion of the leaf part 30B positioned undermost, while the upper end portion of the leaf part 30A positioned topmost.

With the connection structure above, the diameter of the ozone generator body 3-4 can be adjusted by changing the position where the Velcro tape pieces 3a on the leaf part 30A and the Velcro tape pieces 3a on the leaf part 30B are fastened to each other.

The entire ozone generator body 3-4 can also be developed into a planar shape in which the ten leaf parts 30 are arranged laterally by unfastening the Velcro tape pieces 3a, 3a' of all the leaf parts 30.

Figure 27:
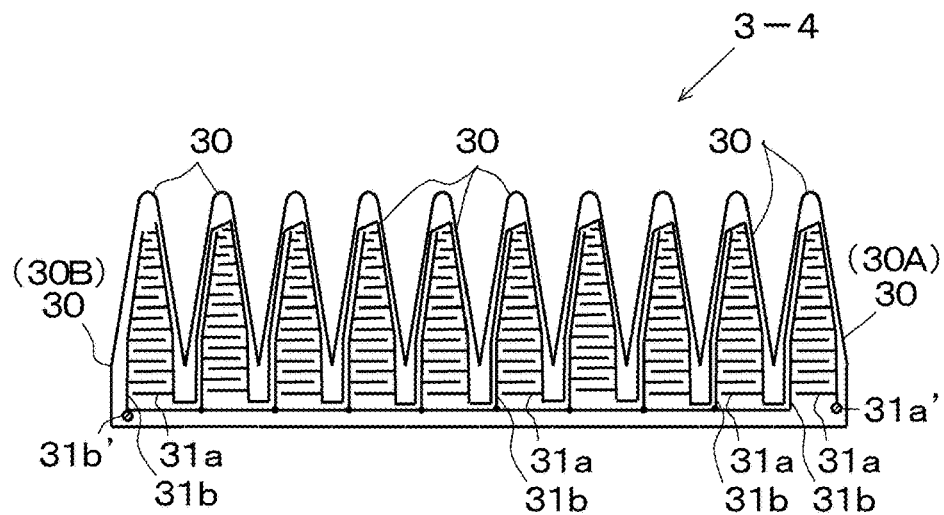
FIG. 27 is a plan view showing the electrical structure of an ozone generator body according to a variation of the sixth embodiment.

FIG. 27 is a plan view showing the electrical structure of an ozone generator body according to a variation of the sixth embodiment.

As shown in FIG. 27, the headgear cleaner 1-6 of this embodiment has an electrical structure in which ten pairs of electrodes 31a, 31b are connected in parallel to the voltage supply part 5 (see FIG. 25).

That is, the electrodes 31a of adjacent ones of the leaf parts 30 are connected sequentially and adjacent ones of the electrodes 31b are also connected sequentially. Then, a terminal 31a' of the leaf part 30A is connected to the wire 5a of the voltage supply part 5 (see FIG. 5, for example), while a terminal 31b' of the leaf part 30B is connected to the wire 5b of the voltage supply part 5.

Since the other configurations, operations, and effects are the same as those in the above-described first to fifth embodiments, the description thereof will be omitted.

Seventh Embodiment

Next will be described a seventh embodiment of the present invention.

Figure 28:
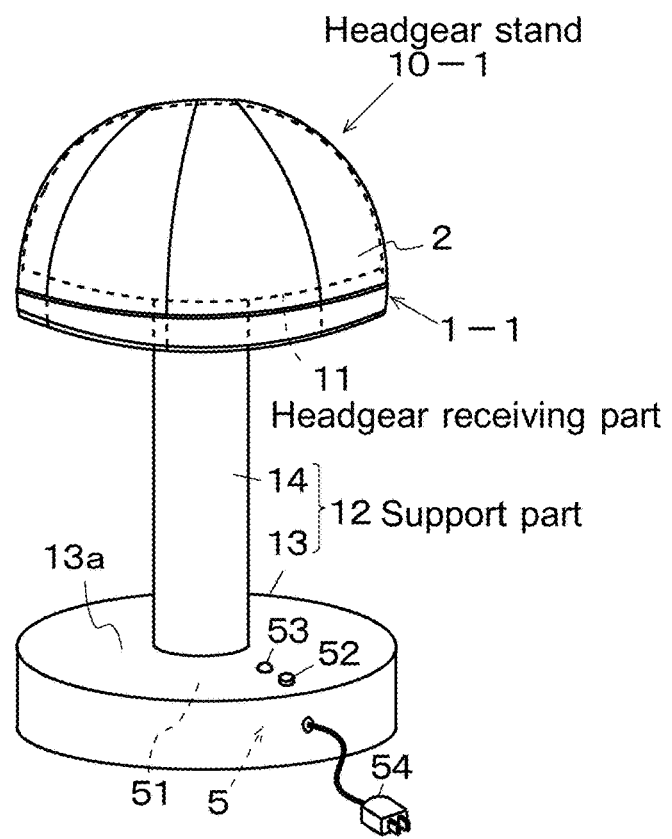
FIG. 28 is a perspective view showing a headgear stand according to a seventh embodiment of the present invention.
Figure 29:
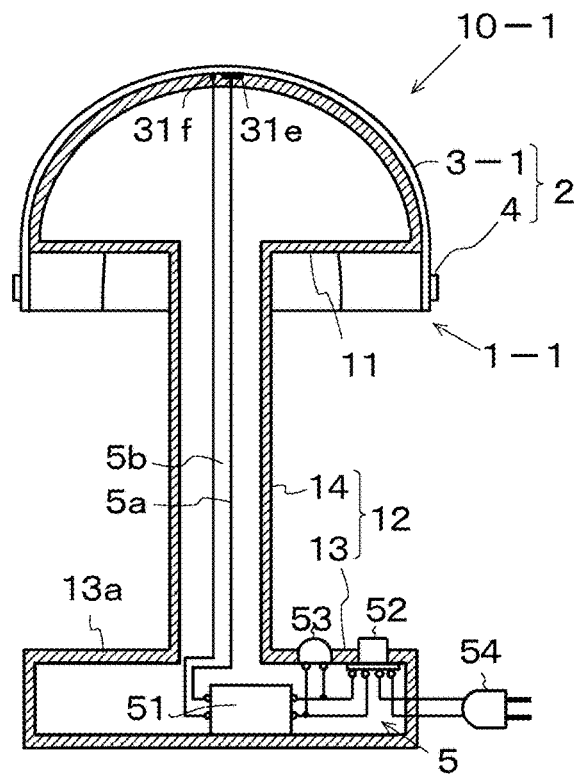
FIG. 29 is a schematic cross-sectional view showing the headgear stand.

FIG. 28 is a perspective view showing a headgear stand according to the seventh embodiment of the present invention and FIG. 29 is a schematic cross-sectional view showing the headgear stand.

As shown in FIG. 28, the headgear stand 10-1 of this embodiment is composed of headgear receiving part 11, a support part 12, and a headgear cleaner 1-1 of the first embodiment.

The headgear receiving part 11 is an approximately semi-spherical cavity capable of receiving a helmet 100 (see FIG. 1) thereon.

The support part 12 is a self-standing body that supports the headgear receiving part 11 at the upper end and formed by a circular base portion 13 and a cylindrical portion 14 provided in a manner standing at the center on the upper surface of the base portion 13.

The ozone generator 2 of the headgear cleaner 1-1 is put and fixed on the headgear receiving part 11, and the voltage supply part 5 is assembled into the base portion 13 of the support part 12.

Specifically, as shown in FIG. 29, the boosting circuit 51 of the voltage supply part 5 is arranged in a central portion of the base portion 13, and the switch 52 and the LED lamp 53, which are connected electrically to the boosting circuit 51, are attached to the top surface 13a of the base portion 13. The plug 54 is then arranged external to the base portion 13, and an end portion of the plug 54 is connected to the switch 52 within the base portion 13.

On the other hand, the wires 5a, 5b extending out of the boosting circuit 51 are connected electrically through the cylindrical portion 14 of the support part 12 to the terminals 31e, 31f (see FIGS. 5 and 6) in the central portion on the inner surface of the ozone generator 2, respectively.

With the arrangement above, when a helmet 100 is put on the headgear receiving part 11 with the support part 12 standing, the ozone generator 2 of the headgear cleaner 1-1 is arranged inside of the helmet 100, so that the helmet 100 is held reliably on the headgear receiving part 11.

In this state, when the switch 52 of the voltage supply part 5 is turned on to activate the boosting circuit 51, a predetermined voltage is supplied from the boosting circuit 51 to the twelve pairs of electrodes 31a, 31b (see FIGS. 3 and 4) of the ozone generator 2, whereby ozone is released from the ozone generator 2.

As a result, ozone is released against the inner surface of the helmet 100, whereby the interior of the helmet 100 is to be sterilized and deodorized.

Since the other configurations, operations, and effects are the same as those in the above-described first to fifth embodiments, the description thereof will be omitted.

Eighth Embodiment

Next will be described an eighth embodiment of the present invention.

Figure 30:
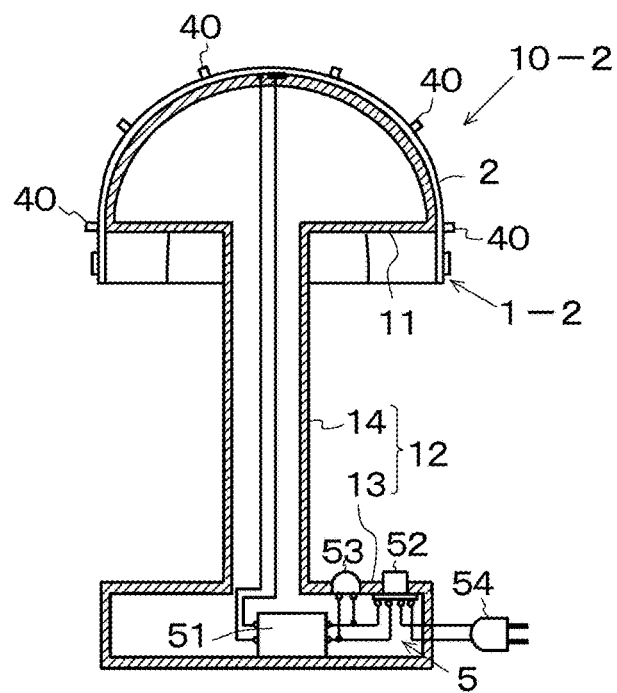
FIG. 30 is a schematic cross-sectional view showing a headgear stand according to an eighth embodiment of the present invention.

FIG. 30 is a schematic cross-sectional view showing a headgear stand according to an eighth embodiment of the present invention.

As shown in FIG. 30, the headgear stand 10-2 of this embodiment is composed of headgear receiving part 11, a support part 12, and a headgear cleaner 1-2 of the second embodiment.

That is, the ozone generator 2, having multiple protruding spacers 40 on the surface thereof is put on the headgear receiving part 11, and the voltage supply part 5 is assembled into the base portion 13 of the support part 12.

Since the other configurations, operations, and effects are the same as those in the above-described first to seventh embodiments, the description thereof will be omitted.

Ninth Embodiment

Next will be described a ninth embodiment of the present invention.

Figure 31:
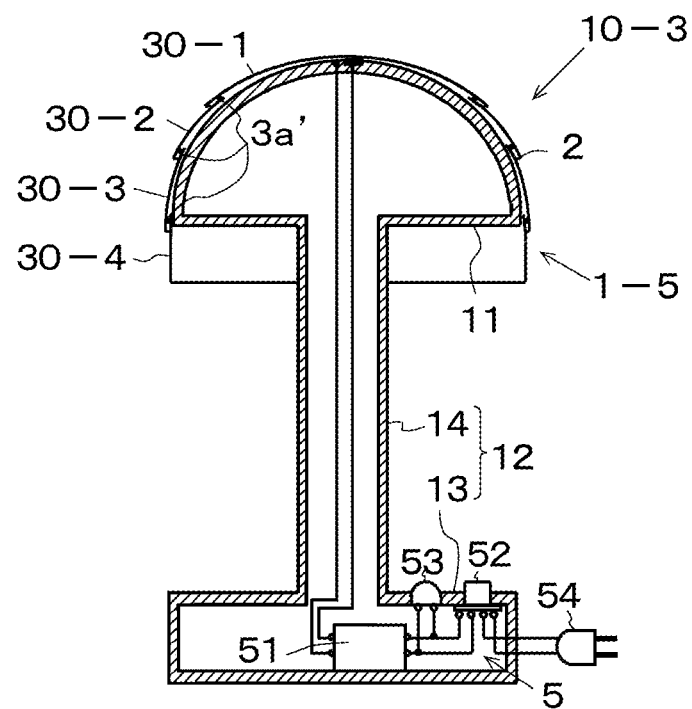
FIG. 31 is a schematic cross-sectional view showing a headgear stand according to a ninth embodiment of the present invention.

FIG. 31 is a schematic cross-sectional view showing a headgear stand according to a ninth embodiment of the present invention.

As shown in FIG. 31, the headgear stand 10-3 of this embodiment is composed of headgear receiving part 11, a support part 12, and a headgear cleaner 1-5 of the fifth embodiment.

That is, the ozone generator 2, formed by a top part 30-1, three annular parts 30-2 to 30-4, and multiple Velcro tape pieces 3a', is put on the headgear receiving part 11, and the voltage supply part 5 is assembled into the base portion 13 of the support part 12.

Since the other configurations, operations, and effects are the same as those in the above-described first to eighth embodiments, the description thereof will be omitted.

It is noted that the present invention is not intended to be limited to the above-described embodiments, but may be variously varied and changed within the spirit and scope of the invention.

For example, while in the above-described embodiments, an AC commercial power supply is applied as a power supply for boosting through the boosting circuit 51, headgear cleaners and headgear stands that use a battery as a power supply are also included in the scope of the present invention.

While the ozone generators applied in the above-described first to third, fifth, and sixth embodiments employ a configuration in which a pair of comb-shaped electrodes 31a, 31b are both housed in the dielectric 32, and the ozone generator body applied in the fourth embodiment employs a configuration in which one electrode 31a is housed in the dielectric 32, while the other electrode 31b is provided on the upper surface of the dielectric 32. The ozone generator body is not limited to such configurations, but may be arranged, for example, such that each pair of electrodes 31a, 31b are formed in a plate shape and arranged laterally at regular intervals.

While the above-described embodiments show a case where multiple pairs of electrodes 31a, 31b are connected in parallel to the voltage supply part 5, headgear cleaners and headgear stands having a structure in which multiple pairs of electrodes 31a, 31b are connected in series to the voltage supply part 5 are also included in the scope of the present invention.

Also, in the above-described embodiments, the structure is exemplified in which multiple pairs of electrodes 31a, 31b are connected in parallel to the voltage supply part 5 via the terminals 31c, 31d, 31e, 31f, but may be configured in any other way without limiting thereto.

Further, in the above-described first to fourth embodiments, a belt-shaped body is exemplified as a connecting part 4, though not limited to such a belt-shaped body. For example, multiple Velcro tape pieces 3a may be applied as a connecting part.

Figure 32:
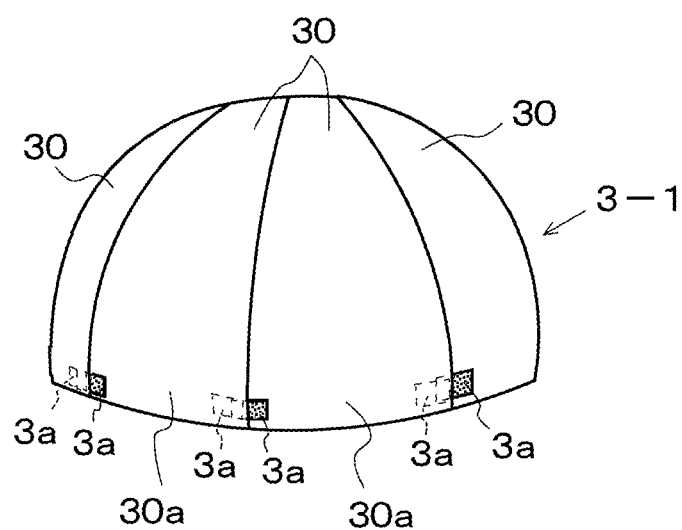
FIG. 32 is a perspective view showing a variation of a connecting part.

That is, as shown in FIG. 32, Velcro tape pieces 3a, for example, are preliminarily attached to the left corner on the exterior surface and the right corner on the interior surface in the lower end portion 30a of each leaf part 30 of the ozone generator body 3-1. The overall shape of the ozone generator body 3-1 can then be kept in an approximately semispherical hull shape by fastening the Velcro tape piece 3a in the left corner on the exterior surface of one of adjacent leaf parts 30 and the Velcro tape piece 3a in the right corner on the interior surface of the other leaf part 30. The size of the ozone generator body 3-1 can also be adjusted by adjusting the position where the Velcro tape pieces 3a are fastened to each other.

Further, in the above-described sixth embodiment, the upper end portions of all the leaf parts 30 of the ozone generator body 3-4 are collected and connected at the top portion O by Velcro tape pieces 3a', but the connection structure is not limited there to. For example, a pin and a string may be used to collect the upper end portions of all the leaf parts 30 at the top portion O.

While the headgear stands 10-1 to 10-3 of the above-described seventh to ninth embodiments are applied, respectively, with the headgear cleaners 1-1, 1-2, and 1-5 of the first, second, and fifth embodiments, headgear stands with the headgear cleaners 1-3 and 1-4 of the third, fourth, and sixth embodiments applied thereto are also included in the scope of the present invention.

REFERENCE SIMS LIST 1-1 to 1-6 . . . headgear cleaner, 2 . . . ozone generator, 3a, 3a' . . . Velcro tape piece, 3b . . . surface, 3-1 to 3-4 . . . ozone generator body, 4 . . . connecting part, 4a . . . Velcro tape, 5a, 5b . . . wire, 5, 5-1 to 5-3 . . . voltage supply part, 10-1 to 10-3 . . . headgear stand, 11 . . . headgear receiving part, 12 . . . support part, 13 . . . base portion, 13a . . . top surface, 14 . . . cylindrical portion, 30 . . . leaf part, 30a . . . lower end portion, 30c . . . opening, 30d . . . upper opening portion, 30e . . . lower opening portion, 30-2 to 30-4 . . . annular part, 30-1 . . . top part, 31a, 31b . . . electrode, 31a', 31b' . . . terminal portion, 31b1 . . . circular hole, 31c to 31f, 31c1 to 31c3, 31e1 to 31e3, 31f1 to 31f3 . . . terminal, 32 . . . dielectric, 32a' . . . via hole, 32a, 32b . . . dielectric layer, 33 . . . base material, 35 . . . protective layer, 40 to 44 . . . spacer, 50 . . . case body, 51 . . . boosting circuit, 51a, 51b . . . output terminal, 52 . . . switch, 53 . . . lamp, 54 . . . plug, 55 . . . timer, 100 . . . helmet, 101 . . . inner surface, 0 . . . central portion (top portion), h . . . height, S . . . gap, K . . . bacteria, B . . . culture medium, $O_3$ . . . ozone

The invention claimed is:

1. A headgear cleaner comprising: an approximately semi-spherical hull-shaped ozone generator formed of flexible material and capable of receiving headgear such as a helmet thereon; and a voltage supply part for supplying a voltage required to generate ozone to the ozone generator, wherein
the ozone generator has a dielectric and one or more pairs of electrodes,
at least one electrode of each pair of electrodes is covered with the dielectric, and
the voltage supply part is arranged to supply a voltage required to generate ozone to the one or more pairs of electrodes of the ozone generator, and wherein
the ozone generator comprises: multiple leaf parts extending radially from a top portion and curved downward to have an approximately semispherical hull shape as a whole; and a connecting part that is connected to lower end portions of the multiple circularly arranged leaf parts to keep the overall shape of the multiple leaf parts in the approximately semispherical hull shape.

2. The headgear cleaner according to claim 1, wherein the ozone generator can be developed, by detaching the connecting part, into a planar shape in which the multiple leaf parts extend radially from a central portion that corresponds to the top portion.

3. A headgear cleaner comprising: an approximately semispherical hull-shaped ozone generator formed of flexible material and capable of receiving headgear such as a helmet thereon; and a voltage supply part for supplying a voltage required to generate ozone to the ozone generator, wherein
the ozone generator has a dielectric and one or more pairs of electrodes,
at least one electrode of each pair of electrodes is covered with the dielectric, and
the voltage supply part is arranged to supply a voltage required to generate ozone to the one or more pairs of electrodes of the ozone generator, and wherein
the ozone generator comprises: multiple leaf parts having multiple circularly connected lower end portions and curved upward to have an approximately semispherical hull shape as a whole; and a connecting part that connects all upper end portions of the multiple leaf parts at a top portion and connects specific adjacent ones of the leaf parts to keep the overall shape of the multiple leaf parts in the approximately semispherical hull shape.

4. The headgear cleaner according to claim 3, wherein the ozone generator can be developed, by detaching the connecting part, into a planar shape in which the multiple leaf parts are arranged laterally with the multiple lower end portions connected.

5. A headgear cleaner comprising: an approximately semispherical hull-shaped ozone generator formed of flexible material and capable of receiving headgear such as a helmet thereon; and a voltage supply part for supplying a voltage required to generate ozone to the ozone generator, wherein
the ozone generator has a dielectric and one or more pairs of electrodes,
at least one electrode of each pair of electrodes is covered with the dielectric, and
the voltage supply part is arranged to supply a voltage required to generate ozone to the one or more pairs of electrodes of the ozone generator, and wherein
the ozone generator comprises multiple annular parts and a connecting part connecting the annular parts,
the annular parts are each set to have a lower opening portion with a size greater than that of an upper opening portion,
the lower opening portion of an upper one of the annular parts is set to have a size approximately equal to that of the upper opening portion of a lower one of the annular parts that is connected to the upper annular part,
the multiple annular parts are disposed in series downward from a top portion with the lower opening portion of the upper annular part fitted on the upper opening portion of the lower annular part, and
the connecting part connects the upper annular part and the lower annular part in a manner movable up and down.

6. The headgear cleaner according to claim 1, wherein the dielectric of the ozone generator is formed of polymeric resin having a permittivity equal to or higher than 3 and a dielectric breakdown voltage equal to or higher than 15 kV/mm.

7. The headgear cleaner according to claim 1, wherein a spacer is provided on the surface of the ozone generator for keeping the distance between the surface of the ozone generator and the inner surface of the headgear equal to or smaller than 10 mm.

8. The headgear cleaner according to claim 7, wherein the spacer is a protrusion provided in a manner protruding from the surface of the ozone generator and having a height equal to or smaller than 10 mm.

9. The headgear cleaner according to claim 7, wherein the spacer is a linear object attached to the surface of the ozone generator and having a height equal to or smaller than 10 mm.

10. The headgear cleaner according to claim 1, wherein the pair of electrodes of the ozone generator are each formed in a comb shape and comb teeth of each of the pair of electrodes are engaged with each other at regular intervals.

11. The headgear cleaner according to claim 1, wherein one electrode of each pair of electrodes of the ozone generator is housed in the dielectric, while the other electrode, having a number of holes or a comb shape, is disposed on the dielectric facing the one electrode.

12. A headgear cleaner comprising: an approximately semispherical hull-shaped ozone generator formed of flexible material and capable of receiving headgear such as a helmet thereon; and a voltage supply part for supplying a voltage required to generate ozone to the ozone generator, wherein
the ozone generator has a dielectric and one or more pairs of electrodes,
at least one electrode of each pair of electrodes is covered with the dielectric, and
the voltage supply part is arranged to supply a voltage required to generate ozone to the one or more pairs of electrodes of the ozone generator, and wherein
a spacer is provided on the surface of the ozone generator for keeping the distance between the surface of the ozone generator and the inner surface of the headgear equal to or smaller than 10 mm.

13. The headgear cleaner according to claim 12, wherein the spacer is a protrusion provided in a manner protruding from the surface of the ozone generator and having a height equal to or smaller than 10 mm.

14. The headgear cleaner according to claim 12, wherein the spacer is a linear object attached to the surface of the ozone generator and having a height equal to or smaller than 10 mm.

15. The headgear cleaner according to claim 12, wherein the pair of electrodes of the ozone generator are each formed in a comb shape and comb teeth of each of the pair of electrodes are engaged with each other at regular intervals.

16. The headgear cleaner according to claim 12, wherein one electrode of each pair of electrodes of the ozone generator is housed in the dielectric, while the other electrode, having a number of holes or a comb shape, is disposed on the dielectric facing the one electrode.

17. The headgear cleaner according to claim 12, wherein the dielectric of the ozone generator is formed of polymeric resin having a permittivity equal to or higher than 3 and a dielectric breakdown voltage equal to or higher than 15 kV/mm.

* * * * *